(12) United States Patent  
Ouyang et al.

(10) Patent No.: US 11,944,267 B2  
(45) Date of Patent: Apr. 2, 2024

(54) DISPOSABLE ENDOSCOPY CANNULA WITH INTEGRATED GRASPER

(71) Applicant: UroViu, Corp., Bellevue, WA (US)

(72) Inventors: Xiaolong Ouyang, Bellevue, WA (US); Shih-Ping Wang, Los Altos, CA (US)

(73) Assignee: UroViu Corp., Bellevue, WA (US)

( * ) Notice: Subject to any disclaimer, the term of this patent is extended or adjusted under 35 U.S.C. 154(b) by 0 days.

(21) Appl. No.: 17/583,095

(22) Filed: Jan. 24, 2022

(65) Prior Publication Data

US 2022/0211252 A1 Jul. 7, 2022

Related U.S. Application Data

(63) Continuation-in-part of application No. PCT/US2020/046018, filed on Aug. 12, 2020.

(Continued)

(51) Int. Cl.
*A61B 1/00* (2006.01)
*A61B 1/018* (2006.01)
(Continued)

(52) U.S. Cl.
CPC ...... *A61B 1/00103* (2013.01); *A61B 1/00052* (2013.01); *A61B 1/00066* (2013.01);
(Continued)

(58) Field of Classification Search
CPC ............ A61B 1/00052; A61B 1/00066; A61B 1/00087; A61B 1/00103; A61B 1/00105;
(Continued)

(56) References Cited

U.S. PATENT DOCUMENTS 4,005,714 A * 2/1977 Hiltebrandt ........ A61B 18/1442  
606/51  
4,016,881 A * 4/1977 Rioux ................ A61B 18/1442  
606/42

(Continued)

FOREIGN PATENT DOCUMENTS

CN 102858275 1/2013  
CN 105636621 6/2016  
(Continued)

OTHER PUBLICATIONS

International Search Report and Written Opinion of PCT/US2016/18670, dated Jul. 12, 2016.

(Continued)

*Primary Examiner* — Ryan N Henderson  
(74) *Attorney, Agent, or Firm* — Wissing Miller LLP

(57) ABSTRACT

An endoscopic system includes an integrated grasper device passing through a device lumen in the cannula. The grasper device has distal end forming two jaw portions that are biased to remain in an open position if unconstrained. The grasper has arch shaped portions that push against the inner surface of the device lumen when the grasper is retracted. To close the jaws of the grasper the grasper is retracted proximally until the arch shaped portions engage the opening of the device lumen. Further retraction causes the grasper jaws to close through engagement with the device lumen inner surface. The endoscopy system can include a single-use, removable cannula having a camera module on its distal tip. A re-usable portion can include the hand piece and display screen.

10 Claims, 12 Drawing Sheets

Related U.S. Application Data

(60) Provisional application No. 63/044,358, filed on Jun. 26, 2020, provisional application No. 63/044,959, filed on Jun. 26, 2020, provisional application No. 63/001,362, filed on Mar. 29, 2020, provisional application No. 62/978,507, filed on Feb. 19, 2020, provisional application No. 62/955,859, filed on Dec. 31, 2019, provisional application No. 62/933,490, filed on Nov. 10, 2019, provisional application No. 62/901,393, filed on Sep. 17, 2019, provisional application No. 62/897,352, filed on Sep. 8, 2019, provisional application No. 62/884,688, filed on Aug. 9, 2019, provisional application No. 62/880,677, filed on Jul. 31, 2019, provisional application No. 62/878,384, filed on Jul. 25, 2019.

(51) Int. Cl.
*A61B 10/02* (2006.01)
*A61B 10/04* (2006.01)
*A61B 10/06* (2006.01)
*A61B 17/29* (2006.01)
*A61B 1/015* (2006.01)
*A61B 17/00* (2006.01)
*A61B 17/30* (2006.01)
*A61M 5/32* (2006.01)

(52) U.S. Cl.
CPC ...... *A61B 1/00087* (2013.01); *A61B 1/00105* (2013.01); *A61B 1/00128* (2013.01); *A61B 1/018* (2013.01); *A61B 10/0291* (2013.01); *A61B 10/04* (2013.01); *A61B 10/06* (2013.01); *A61B 17/29* (2013.01); *A61B 1/015* (2013.01); *A61B 2017/0023* (2013.01); *A61B 2017/0034* (2013.01); *A61B 2017/0046* (2013.01); *A61B 2017/305* (2013.01); *A61B 2217/005* (2013.01); *A61B 2217/007* (2013.01); *A61M 5/32* (2013.01)

(58) Field of Classification Search
CPC ..... A61B 1/00128; A61B 1/012; A61B 1/015; A61B 1/018; A61B 1/0052; A61B 2017/0023; A61B 2017/0034; A61B 2017/0046; A61B 2017/305; A61B 2217/005; A61B 2217/007; A61M 5/32
See application file for complete search history.

(56) References Cited

U.S. PATENT DOCUMENTS

| | | | |
|---|---|---|---|
| 4,222,380 A * | 9/1980 | Terayama | A61M 25/0084 604/164.01 |
| 4,418,692 A * | 12/1983 | Guay | A61B 18/1442 606/45 |
| 4,854,302 A | 8/1989 | Allred, III | |
| 4,979,497 A | 12/1990 | Matsura | |
| 5,010,876 A | 4/1991 | Henley | |
| 5,188,093 A | 2/1993 | Lafferty | |
| 5,237,984 A | 8/1993 | Williams, II | |
| 5,281,214 A | 1/1994 | Wilkins | |
| 5,323,767 A | 6/1994 | Lafferty | |
| 5,329,936 A | 7/1994 | Lafferty | |
| 5,456,683 A * | 10/1995 | Fritzsch | A61B 18/1442 606/41 |
| 5,474,057 A | 12/1995 | Makower | |
| 5,486,155 A | 1/1996 | Muller | |
| 5,527,313 A * | 6/1996 | Scott | A61B 18/1442 606/41 |
| 5,527,332 A | 6/1996 | Clement | |
| 5,549,547 A | 8/1996 | Cohen | |
| 5,569,163 A | 10/1996 | Francis | |
| 5,578,030 A | 11/1996 | Levin | |
| 5,611,813 A * | 3/1997 | Lichtman | A61B 18/1445 606/174 |
| 5,636,639 A * | 6/1997 | Turturro | A61B 10/0266 600/564 |
| 5,666,561 A | 9/1997 | Stephenson | |
| 5,667,472 A | 9/1997 | Finn | |
| 5,667,476 A | 9/1997 | Frassica et al. | |
| 5,683,388 A * | 11/1997 | Slater | A61B 10/06 606/41 |
| 5,782,747 A * | 7/1998 | Zimmon | A61B 17/29 600/101 |
| 5,785,644 A | 7/1998 | Grabover | |
| 5,860,953 A | 1/1999 | Snoke | |
| 5,873,814 A | 2/1999 | Adair | |
| 5,895,361 A | 4/1999 | Turturro | |
| 5,928,137 A | 7/1999 | Green | |
| 5,935,141 A | 8/1999 | Weldon | |
| 5,957,947 A | 9/1999 | Wattiez | |
| 5,984,939 A * | 11/1999 | Yoon | A61B 18/1442 606/205 |
| 6,007,531 A | 12/1999 | Snoke | |
| 6,007,546 A | 12/1999 | Snow | |
| 6,017,322 A | 1/2000 | Snoke | |
| 6,033,378 A | 3/2000 | Lundquist | |
| 6,059,719 A | 5/2000 | Yamamato et al. | |
| 6,095,970 A | 8/2000 | Hidaka | |
| 6,110,127 A * | 8/2000 | Suzuki | A61B 10/06 606/205 |
| 6,174,307 B1 | 1/2001 | Daniel | |
| 6,210,416 B1 | 4/2001 | Chu | |
| 6,211,904 B1 | 4/2001 | Adair | |
| 6,221,007 B1 | 4/2001 | Green | |
| 6,221,070 B1 | 4/2001 | Tu et al. | |
| 6,261,226 B1 | 7/2001 | McKenna | |
| 6,280,386 B1 | 8/2001 | Alfano | |
| 6,319,195 B1 * | 11/2001 | Nakaichi | A61B 1/267 600/150 |
| 6,331,174 B1 | 12/2001 | Reinhard | |
| 6,387,043 B1 | 5/2002 | Yoon | |
| 6,398,743 B1 | 6/2002 | Halseth | |
| 6,507,699 B2 | 1/2003 | Lemoine | |
| 6,518,823 B1 | 2/2003 | Kawai | |
| 6,673,087 B1 | 1/2004 | Chang | |
| 6,793,882 B1 | 9/2004 | Verschuur | |
| 6,917,380 B1 | 7/2005 | Tay | |
| 7,169,167 B2 * | 1/2007 | Chu | A61B 17/29 606/205 |
| 7,256,446 B2 | 8/2007 | Hu | |
| 7,428,378 B1 | 9/2008 | Warpakowski | |
| 7,507,205 B2 | 3/2009 | Borovsky | |
| 7,591,799 B2 | 9/2009 | Selkee | |
| 7,606,609 B2 | 10/2009 | Muranushi | |
| 7,780,650 B2 | 8/2010 | Frassica | |
| 7,798,995 B2 | 9/2010 | Yue | |
| 7,931,616 B2 | 4/2011 | Selkee | |
| 7,946,981 B1 | 5/2011 | Cubb | |
| 8,057,464 B2 | 9/2011 | Chen | |
| 8,052,609 B2 | 11/2011 | Harhen | |
| 8,187,171 B2 | 5/2012 | Irion | |
| 8,197,398 B2 | 6/2012 | Scholly | |
| 8,235,975 B2 | 8/2012 | Chen | |
| 8,361,775 B2 | 4/2013 | Flower | |
| 8,460,182 B2 | 6/2013 | Ouyang | |
| 8,523,808 B2 | 9/2013 | Selkee | |
| 8,696,552 B2 | 4/2014 | Whitman | |
| 8,803,960 B2 | 8/2014 | Sonnenschein | |
| 8,834,357 B2 | 9/2014 | Oskin | |
| 8,845,522 B2 | 9/2014 | McIntyre | |
| 8,952,312 B2 | 2/2015 | Blanqart | |
| 8,986,221 B2 * | 3/2015 | Zimmon | A61B 10/0266 600/562 |
| 8,998,844 B2 | 4/2015 | Reed | |
| 9,561,046 B2 * | 2/2017 | Murdeshwar | A61B 17/295 |
| 9,649,014 B2 | 5/2017 | Ouyang | |
| 9,736,342 B2 | 8/2017 | Mueckl | |
| 9,795,505 B2 * | 10/2017 | Yu | A61B 1/0057 |
| 9,895,048 B2 | 2/2018 | Ouyang | |

(56) References Cited

U.S. PATENT DOCUMENTS

| | | |
|---|---|---|
| 10,278,563 B2 | 5/2019 | Ouyang |
| 10,292,571 B2 | 5/2019 | Ouyang |
| 10,595,710 B2 | 3/2020 | Gill |
| 10,653,303 B2 * | 5/2020 | Asaoka ............... A61B 1/0057 |
| 11,478,264 B2 * | 10/2022 | Murdeshwar ...... A61B 18/1447 |
| 2001/0007051 A1 | 7/2001 | Nakashima |
| 2001/0049509 A1 | 12/2001 | Sekine |
| 2003/0016284 A1 | 1/2003 | Squilla |
| 2003/0023142 A1 | 1/2003 | Grabover |
| 2003/0078476 A1 | 4/2003 | Hill |
| 2003/0078502 A1 | 4/2003 | Miyaki |
| 2003/0105488 A1 * | 6/2003 | Chu ....................... A61B 17/29 |
| | | 606/205 |
| 2003/0151680 A1 | 8/2003 | McDermott |
| 2003/0199735 A1 | 10/2003 | Dickopp |
| 2004/0054254 A1 | 3/2004 | Miyake |
| 2004/0054259 A1 | 3/2004 | Hasegawa |
| 2004/0138558 A1 | 7/2004 | Dunki-Jacobs |
| 2004/0162572 A1 | 8/2004 | Sauer |
| 2005/0010178 A1 | 1/2005 | Katz |
| 2005/0264687 A1 | 1/2005 | Murayama |
| 2005/0049459 A1 | 3/2005 | Hern |
| 2005/0065397 A1 | 3/2005 | Saadat |
| 2005/0085695 A1 | 4/2005 | Sherner |
| 2005/0154262 A1 | 7/2005 | Banik |
| 2005/0159646 A1 | 7/2005 | Nordstrom |
| 2005/0177027 A1 | 8/2005 | Hirata |
| 2005/0277874 A1 | 12/2005 | Selkee |
| 2005/0277875 A1 | 12/2005 | Selkee |
| 2006/0052710 A1 | 3/2006 | Miura |
| 2006/0063976 A1 | 3/2006 | Aizenfeld |
| 2006/0114986 A1 | 6/2006 | Knapp |
| 2006/0152601 A1 | 7/2006 | Parekh |
| 2006/0167340 A1 | 7/2006 | Peas |
| 2006/0171693 A1 | 8/2006 | Todd |
| 2006/0173245 A1 | 8/2006 | Todd |
| 2006/0184227 A1 | 8/2006 | Rust |
| 2006/0259124 A1 | 11/2006 | Matsuoka |
| 2006/0287576 A1 | 12/2006 | Tsuji |
| 2007/0060789 A1 | 3/2007 | Uchimura |
| 2007/0081920 A1 | 4/2007 | Murphy |
| 2007/0117437 A1 | 5/2007 | Boehnlein |
| 2007/0129604 A1 | 6/2007 | Hatcher |
| 2007/0162095 A1 | 7/2007 | Kimmel |
| 2007/0167678 A1 | 7/2007 | Moskowitz |
| 2007/0167868 A1 | 7/2007 | Sauer |
| 2007/0173693 A1 | 7/2007 | Refael |
| 2007/0187875 A1 | 8/2007 | Terasaki |
| 2007/0188604 A1 | 8/2007 | Miyamoto |
| 2007/0197875 A1 | 8/2007 | Osaka |
| 2007/0210162 A1 | 9/2007 | Keen |
| 2007/0225556 A1 | 9/2007 | Ortiz |
| 2007/0238927 A1 | 10/2007 | Ueno |
| 2007/0249904 A1 | 10/2007 | Amano |
| 2007/0270894 A1 * | 11/2007 | Zimmon ................ A61B 10/06 |
| | | 606/170 |
| 2008/0004642 A1 | 1/2008 | Birk |
| 2008/0071144 A1 | 3/2008 | Kimmel |
| 2008/0097550 A1 | 4/2008 | Dicks |
| 2008/0108869 A1 | 5/2008 | Sanders |
| 2008/0195125 A1 | 8/2008 | Orbay |
| 2008/0195128 A1 | 8/2008 | Orbay |
| 2008/0225410 A1 | 9/2008 | Ning |
| 2008/0234547 A1 | 9/2008 | Irion et al. |
| 2008/0255416 A1 | 10/2008 | Gilboa |
| 2008/0262306 A1 | 10/2008 | Kawai |
| 2008/0300456 A1 | 12/2008 | Irion |
| 2009/0027489 A1 | 1/2009 | Takemura |
| 2009/0065565 A1 | 3/2009 | Lemoine |
| 2009/0076321 A1 | 3/2009 | Suyama |
| 2009/0076328 A1 | 3/2009 | Root |
| 2009/0080214 A1 | 3/2009 | Watanabe |
| 2009/0105538 A1 | 4/2009 | Van Dam |
| 2009/0118580 A1 | 5/2009 | Sun |
| 2009/0118641 A1 | 5/2009 | Van Dam |
| 2009/0149713 A1 | 7/2009 | Niida |
| 2009/0225159 A1 | 9/2009 | Schneider |
| 2009/0227897 A1 | 9/2009 | Wendt |
| 2009/0286412 A1 | 11/2009 | Ikeda |
| 2009/0287663 A1 | 11/2009 | Takeuchi |
| 2010/0069834 A1 | 3/2010 | Schultz |
| 2010/0094216 A1 | 4/2010 | Yue |
| 2010/0095969 A1 | 4/2010 | Schwartz |
| 2010/0101569 A1 | 4/2010 | Kim |
| 2010/0121142 A1 | 5/2010 | Ouyang |
| 2010/0157039 A1 | 6/2010 | Sugai |
| 2010/0160914 A1 | 6/2010 | Bastian |
| 2010/0168827 A1 | 7/2010 | Schultz |
| 2010/0191051 A1 | 7/2010 | Miyake |
| 2010/0191053 A1 | 7/2010 | Garcia |
| 2010/0234736 A1 | 9/2010 | Corl |
| 2010/0026201 A1 | 10/2010 | Frangioni |
| 2011/0009694 A1 | 1/2011 | Schultz |
| 2011/0015669 A1 * | 1/2011 | Corcosteugi ........... A61B 17/29 |
| | | 606/207 |
| 2011/0034769 A1 | 2/2011 | Adair |
| 2011/0037876 A1 | 2/2011 | Talbert |
| 2011/0054446 A1 | 3/2011 | Schultz |
| 2011/0092775 A1 | 4/2011 | Deshmukh |
| 2011/0105839 A1 * | 5/2011 | Hoffman ................ A61B 10/06 |
| | | 600/104 |
| 2011/0112622 A1 | 5/2011 | Phan |
| 2011/0124961 A1 * | 5/2011 | Zimmon ............ A61B 1/00105 |
| | | 600/104 |
| 2011/0130627 A1 | 6/2011 | McGrail |
| 2011/0211115 A1 | 9/2011 | Tsai |
| 2011/0213206 A1 | 9/2011 | Boutillette |
| 2011/0245602 A1 | 10/2011 | Brannon |
| 2011/0264191 A1 | 10/2011 | Rothstein |
| 2011/0288482 A1 | 11/2011 | Farrell |
| 2011/0313245 A1 | 12/2011 | Scholly |
| 2012/0016191 A1 | 1/2012 | Ito |
| 2012/0040305 A1 | 2/2012 | Karazivan |
| 2012/0041533 A1 | 2/2012 | Bertolino |
| 2012/0053515 A1 | 3/2012 | Crank |
| 2012/0100729 A1 | 4/2012 | Edidin |
| 2012/0165916 A1 | 6/2012 | Jordan |
| 2012/0178991 A1 | 7/2012 | Clark |
| 2012/0226103 A1 | 9/2012 | Gunday |
| 2012/0236138 A1 | 9/2012 | Liu |
| 2012/0245242 A1 | 9/2012 | Peiffer |
| 2012/0245418 A1 | 9/2012 | Boulais |
| 2012/0253116 A1 | 10/2012 | Sniffin |
| 2012/0259203 A1 | 10/2012 | Devereux |
| 2012/0286020 A1 | 11/2012 | Smith |
| 2012/0289858 A1 | 11/2012 | Ouyang |
| 2013/0006145 A1 | 1/2013 | Toomey |
| 2013/0035553 A1 | 2/2013 | Kongstorum |
| 2013/0046142 A1 | 2/2013 | Remijan |
| 2013/0057667 A1 | 5/2013 | McGrath |
| 2013/0150672 A1 | 6/2013 | Fujitani |
| 2013/0172676 A1 | 7/2013 | Levy |
| 2013/0190561 A1 | 7/2013 | Oskin |
| 2013/0225921 A1 | 8/2013 | Liu |
| 2013/0253402 A1 | 9/2013 | Badawi |
| 2013/0096378 A1 | 10/2013 | Alexander |
| 2013/0289559 A1 | 10/2013 | Reid |
| 2013/0324973 A1 | 12/2013 | Reed |
| 2013/0345514 A1 | 12/2013 | Manion |
| 2014/0022649 A1 | 1/2014 | Echhardt |
| 2014/0107416 A1 | 4/2014 | Bimkrant |
| 2014/0111634 A1 | 4/2014 | Mueckl |
| 2014/0154399 A1 | 6/2014 | Weikart |
| 2014/0180007 A1 | 6/2014 | Edidin |
| 2014/0188211 A1 | 7/2014 | Roeder |
| 2014/0213848 A1 | 7/2014 | Moskowitz |
| 2014/0228634 A1 * | 8/2014 | Zimmon ................ A61B 10/04 |
| | | 600/106 |
| 2014/0228635 A1 | 8/2014 | Tuliakov |
| 2014/0275763 A1 | 9/2014 | King |
| 2014/0296866 A1 | 10/2014 | Salman |
| 2014/0323991 A1 | 10/2014 | Tang |
| 2015/0005575 A1 | 1/2015 | Kobayashi |
| 2015/0011830 A1 | 1/2015 | Hunter |

(56) References Cited

U.S. PATENT DOCUMENTS

| | | |
|---|---|---|
| 2015/0018622 A1 | 1/2015 | Tesar |
| 2015/0018710 A1 | 1/2015 | Furlong |
| 2015/0150441 A1 | 6/2015 | Ouyang |
| 2015/0164313 A1 | 6/2015 | Oyuang |
| 2015/0196197 A1 | 7/2015 | Kienzle |
| 2015/0238175 A1 | 8/2015 | Seiger |
| 2015/0238251 A1 | 8/2015 | Shikhman |
| 2015/0297311 A1 | 10/2015 | Tesar |
| 2016/0073853 A1 | 3/2016 | Venkatesan et al. |
| 2016/0077008 A1 | 3/2016 | Takasu |
| 2016/0174819 A1* | 6/2016 | Ouyang ............. A61B 1/00098 600/105 |
| 2016/0334694 A1 | 11/2016 | Liu |
| 2016/0367119 A1 | 12/2016 | Ouyang |
| 2017/0086651 A1 | 3/2017 | Sato |
| 2017/0181853 A1 | 6/2017 | Rothstein |
| 2017/0018879 A1 | 7/2017 | Ouyang |
| 2017/0188793 A1* | 7/2017 | Ouyang ................. A61B 1/015 |
| 2017/0188795 A1 | 7/2017 | Ouyang |
| 2017/0215699 A1 | 8/2017 | Ouyang |
| 2017/0295347 A1 | 10/2017 | Schneider |
| 2017/0296199 A1* | 10/2017 | Beger ................ A61B 17/1611 |
| 2017/0310858 A1 | 10/2017 | Mueck |
| 2018/0132700 A1 | 5/2018 | Ouyang |
| 2018/0184892 A1 | 7/2018 | Truckai |
| 2018/0235441 A1 | 8/2018 | Huang |
| 2018/0256009 A1* | 9/2018 | Ouyang ............. A61B 1/00048 |
| 2018/0289241 A1 | 10/2018 | Zhou |
| 2019/0029497 A1 | 1/2019 | Mirza |
| 2019/0142262 A1 | 5/2019 | Inglis |
| 2019/0216325 A1 | 7/2019 | Ouyang |
| 2019/0223691 A1 | 7/2019 | Takatsuji |
| 2019/0246873 A1 | 8/2019 | Lu |
| 2019/0246884 A1 | 8/2019 | Lu et al. |
| 2019/0282071 A1 | 9/2019 | Ouyang |
| 2019/0282073 A1 | 9/2019 | Truckai |
| 2019/0320879 A1 | 10/2019 | Langell |
| 2019/0374095 A1 | 12/2019 | Lord |
| 2020/0078086 A1* | 3/2020 | Garcia-Bengochea ...................... A61B 18/1445 |
| 2020/0204776 A1 | 6/2020 | Themelis |
| 2020/0214739 A1 | 7/2020 | Shi |
| 2020/0275827 A1 | 9/2020 | Weise |
| 2020/0383557 A1* | 12/2020 | Sedlacek ................ A61B 1/005 |
| 2021/0052383 A1 | 2/2021 | Rothstein |
| 2021/0228806 A1 | 7/2021 | Streeter |
| 2021/0401277 A1 | 12/2021 | Ouyang |

FOREIGN PATENT DOCUMENTS

| | | |
|---|---|---|
| CN | 106132273 | 11/2016 |
| CN | 110234265 | 9/2019 |
| EP | 1690512 | 8/2006 |
| EP | 2560589 | 4/2010 |
| EP | 3384879 | 4/2011 |
| EP | 2749258 | 7/2014 |
| EP | 3078354 | 10/2016 |
| EP | 2721992 | 4/2018 |
| JP | 2009148420 | 7/2009 |
| WO | 2011133792 | 10/2011 |
| WO | 2012060932 | 5/2012 |
| WO | 2012151073 | 11/2012 |
| WO | 2014031192 | 2/2014 |
| WO | 2014065901 | 5/2015 |
| WO | 2016032729 | 3/2016 |
| WO | 2016040131 | 3/2016 |
| WO | 2016137838 | 9/2016 |
| WO | 2018136950 | 7/2018 |
| WO | 2019237003 | 12/2019 |

OTHER PUBLICATIONS

International Search Report and Written Opinion of PCT/US2018/014880, dated Jun. 6, 2018.
International Search Report and Written Opinion of PCT/US2018/065396, dated Feb. 24, 2017.
International Search Report and Written Opinion of PCT/US2021/050095 dated Dec. 17, 2021.
International Search Report and Written Opinion of PCT/US2019/036060 dated Aug. 27, 2019.
International Search Report and Written Opinion of PCT/US2017/053171 dated Dec. 5, 2017.
International Preliminary Report on Patentability of PCT/US2017/053171 completed on Jul. 1, 2019.
Extended European Search Report of European Patent Application No. EP19816177 completed Feb. 2, 2022.
International Search Report and Written Opinion for PCT/US20/046018, dated Oct. 29, 2020.
Extended European Search Report for EP 20 84 3274, completed Jul. 21, 2023.

* cited by examiner

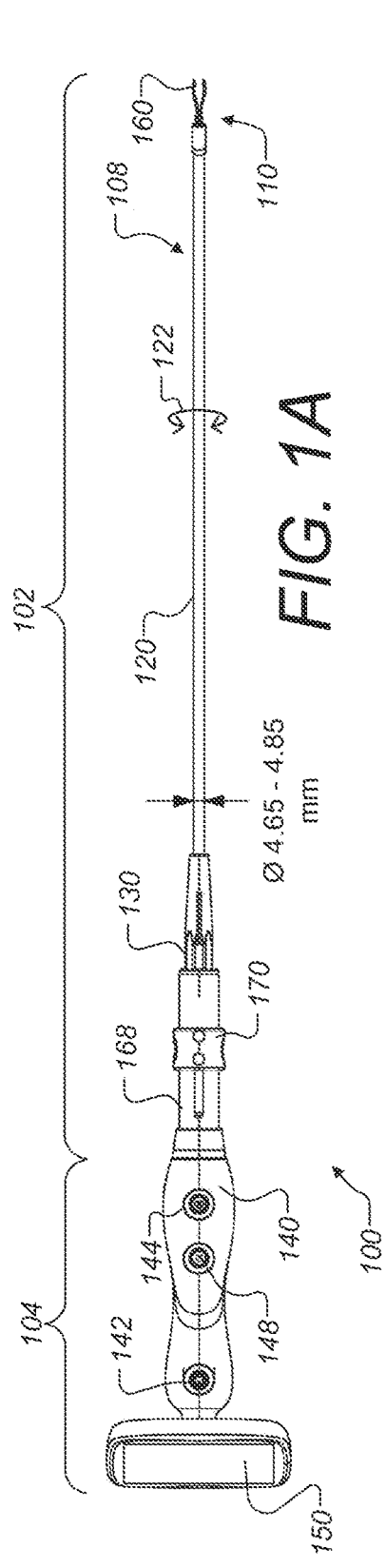
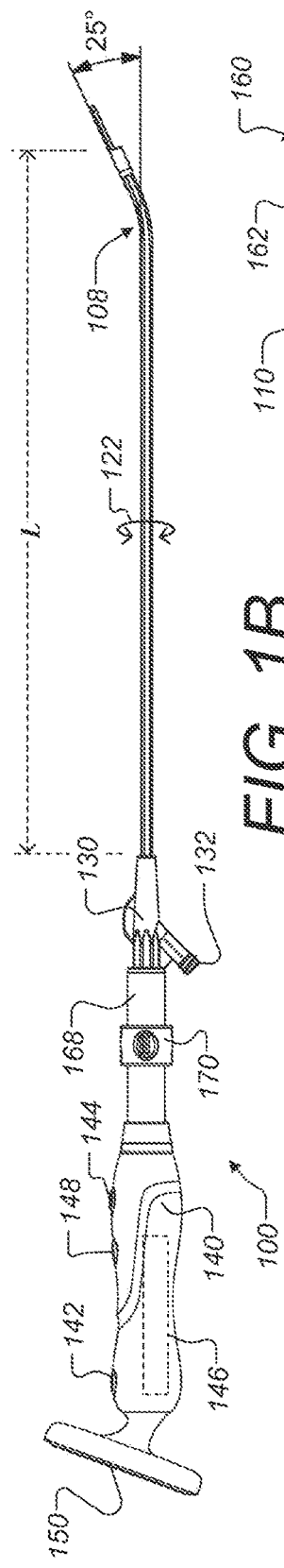
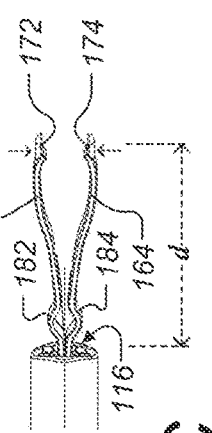
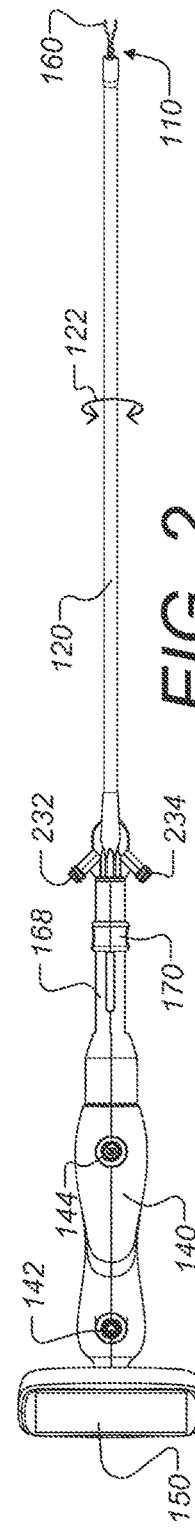
FIG. 1A
FIG. 1B
FIG. 1C
FIG. 2

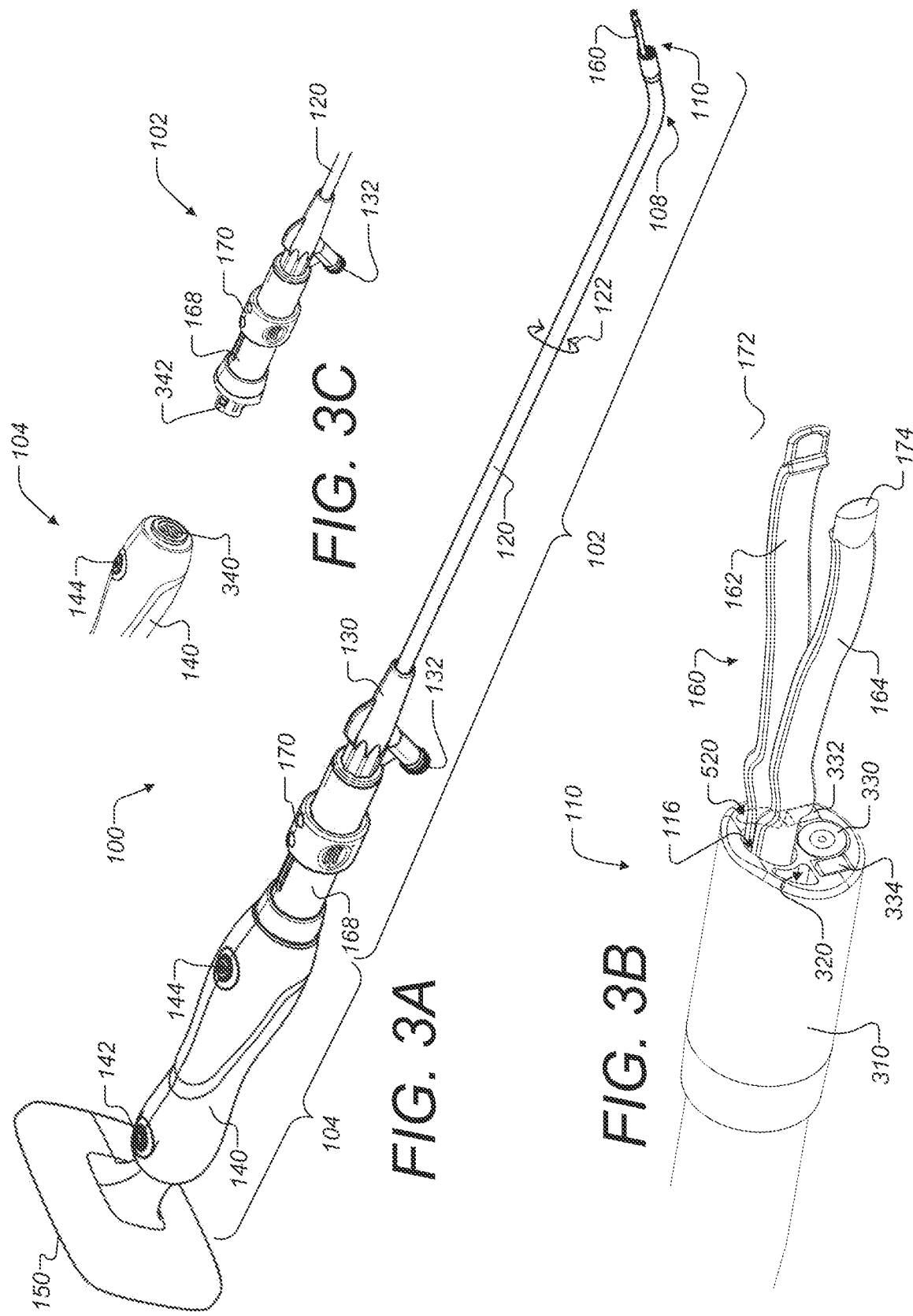

A-A'

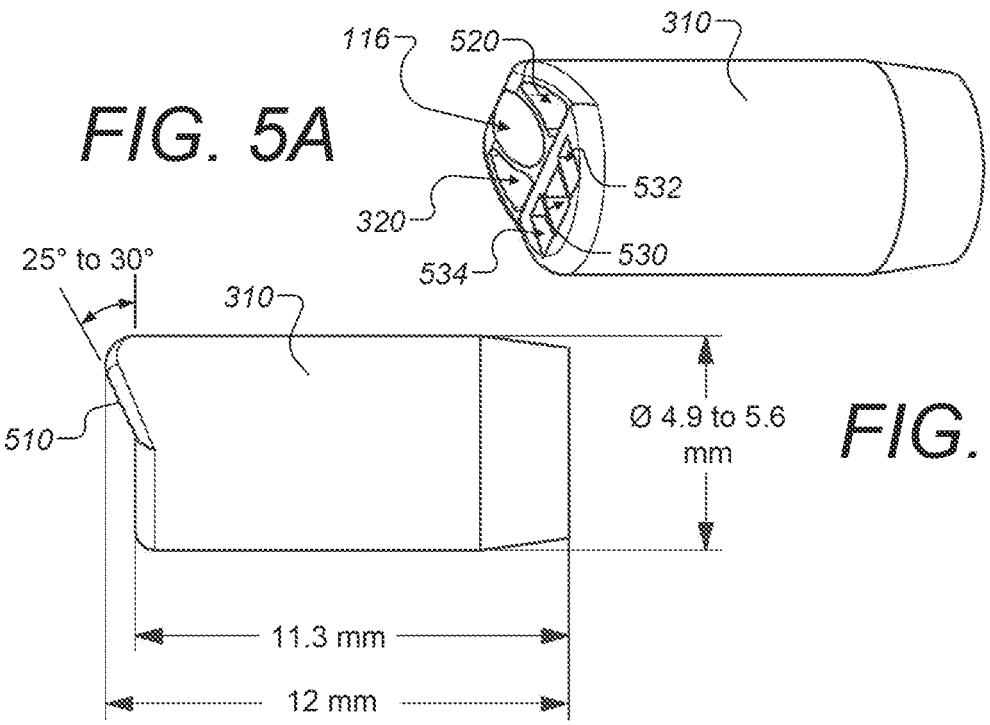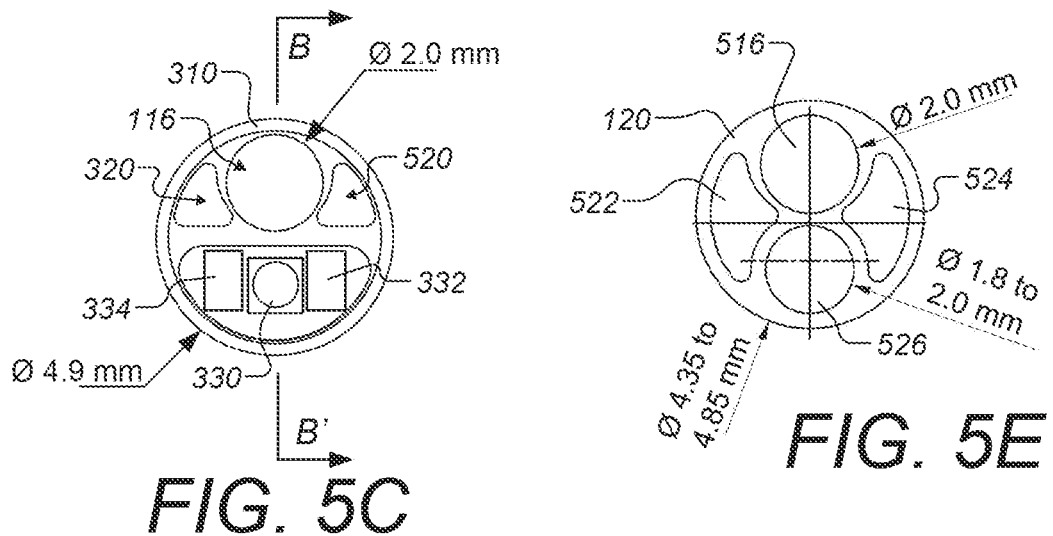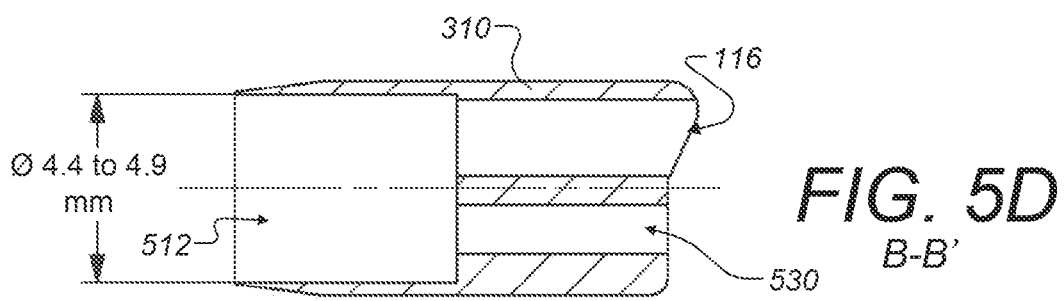

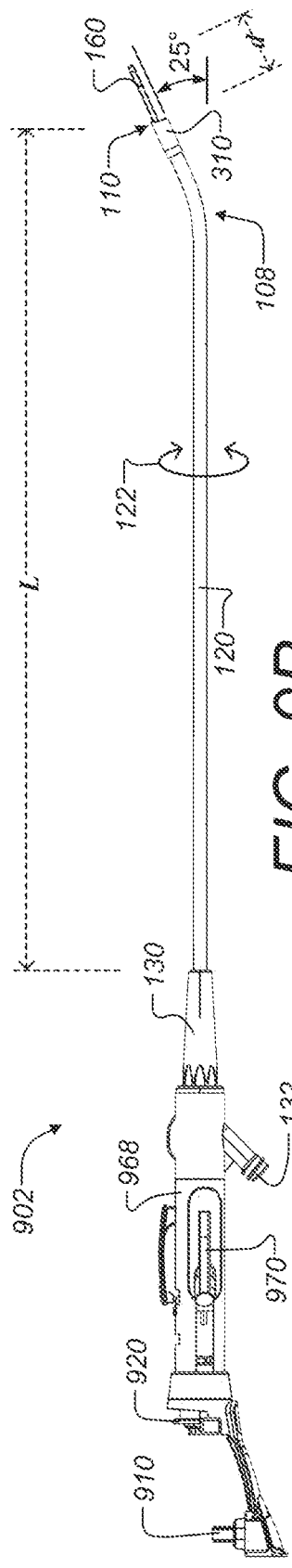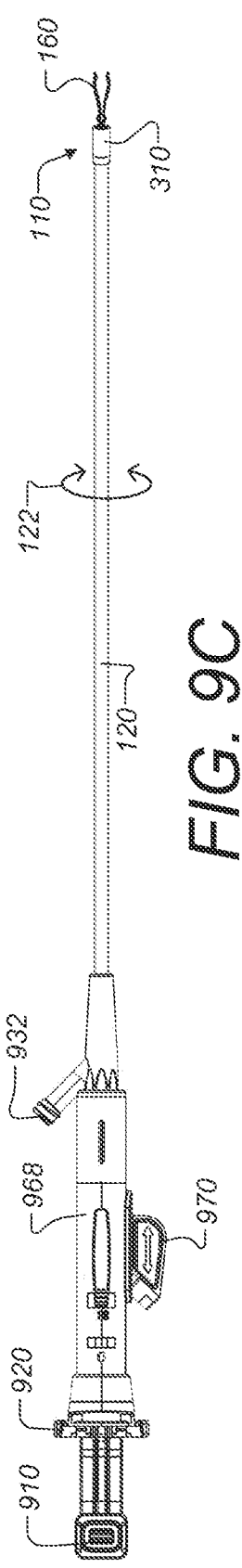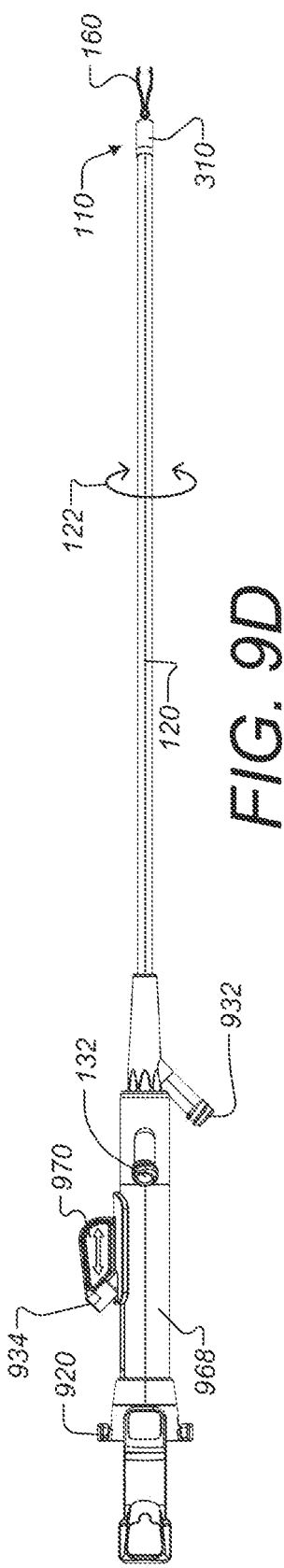

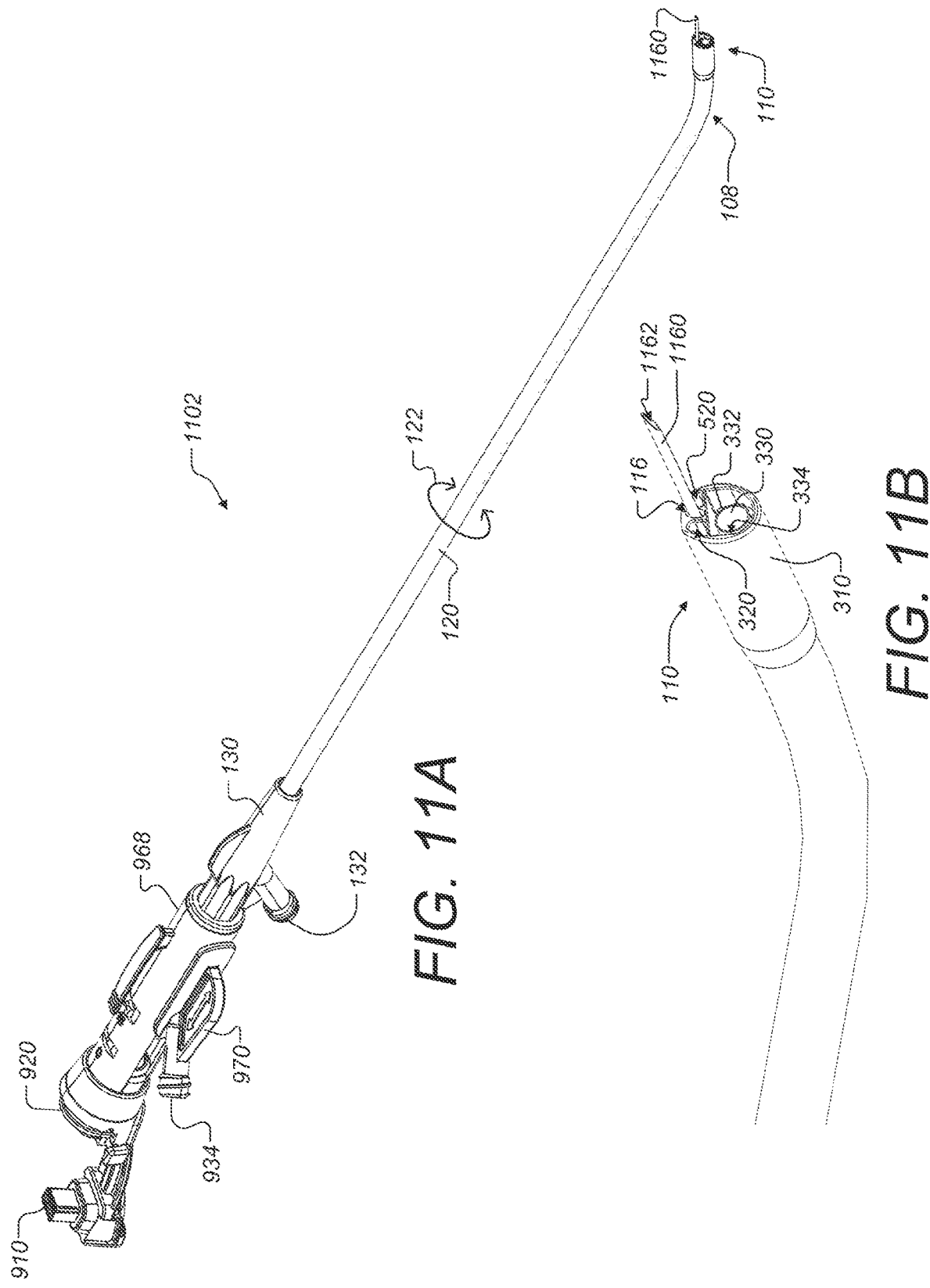

DISPOSABLE ENDOSCOPY CANNULA WITH INTEGRATED GRASPER

REFERENCE TO RELATED APPLICATIONS

This application is a continuation-in part of International Patent Application PCT/US20/046018 filed on Aug. 12, 2020 and published on Jan. 28, 2021 under publication number WO 202/016626. This application incorporates by reference said International Patent Application and each of the U.S. provisional applications to which it claims priority, and claims priority to the International Patent Application and to the U.S. Provisional Patent Applications, namely, U.S. Prov. Ser. No. 63/044,959 filed Jun. 26, 2020;
U.S. Prov. Ser. No. 63/044,358 filed Jun. 26, 2020;
U.S. Prov. Ser. No. 63/001,362 filed Mar. 29, 2020;
U.S. Prov. Ser. No. 62/978,507 filed Feb. 19, 2020;
U.S. Prov. Ser. No. 62/955,859 filed Dec. 31, 2019;
U.S. Prov. Ser. No. 62/933,490 filed Nov. 10, 2019
U.S. Prov. Ser. No. 62/901,393 filed Sep. 17, 2019;
U.S. Prov. Ser. No. 62/897,352 filed Sep. 8, 2019;
U.S. Prov. Ser. No. 62/884,688 filed Aug. 9, 2019;
U.S. Prov. Ser. No. 62/880,677 filed Jul. 31, 2019; and
U.S. Prov. Ser. No. 62/878,384 filed Jul. 25, 2019.

This patent application incorporates by reference each of the following provisional, non-provisional patent applications and issued patent(s):

U.S. Pat. No. 9,895,048 issued Feb. 20, 2018;
U.S. Pat. No. 9,895,858 issued Feb. 20, 2018;
U.S. Pat. No. 10,278,563 issued May 7, 2019;
U.S. Pat. No. 10,292,571 issued May 21, 2019;
U.S. Ser. No. 15/856,077 filed Dec. 28, 2017;
U.S. Ser. No. 16/407,028 filed May 8, 2019;
U.S. Ser. No. 16/413,160 filed May 15, 2019;
U.S. Ser. No. 15/462,331 filed Mar. 17, 2017;
U.S. Ser. No. 14/913,867 filed Feb. 23, 2016;
U.S. Ser. No. 16/664,082 filed Oct. 25, 2019;
Intl. Pat. App. No. PCT/US18/14880 filed Jan. 23, 2018;
Intl. Pat. App. No. PCT/US16/65396 filed Dec. 7, 2016;
Intl. Pat. App. No. PCT/US16/18670 filed Feb. 19, 2016;
U.S. Prov. Ser. No. 62/824,324 filed Mar. 27, 2019;
U.S. Prov. Ser. No. 62/821,536 filed Mar. 21, 2019;
U.S. Prov. Ser. No. 62/587,038 filed Nov. 16, 2017;
U.S. Prov. Ser. No. 62/873,861 filed Jul. 13, 2019.
U.S. Prov. Ser. No. 62/870,748 filed Jul. 4, 2019
U.S. Prov. Ser. No. 62/842,297 filed May 2, 2019;
U.S. Prov. Ser. No. 62/825,948 filed Mar. 29, 2019;
U.S. Prov. Ser. No. 62/821,536 filed Mar. 21, 2019;
U.S. Prov. Ser. No. 62/821,430 filed Mar. 20, 2019;
U.S. Prov. Ser. No. 62/797,235 filed Jan. 26, 2019;
U.S. Prov. Ser. No. 62/796,346 filed Jan. 24, 2019;
U.S. Prov. Ser. No. 62/795,042 filed Jan. 22, 2019;
U.S. Prov. Ser. No. 62/791,045 filed Jan. 11, 2019
U.S. Prov. Ser. No. 62/647,454 filed Mar. 23, 2018;
U.S. Prov. Ser. No. 62/634,854 filed Feb. 24, 2018;
U.S. Prov. Ser. No. 62/587,038 filed Nov. 16, 2017;
U.S. Prov. Ser. No. 62/551,264 filed Aug. 29, 2017;
U.S. Prov. Ser. No. 62/452,883 filed Jan. 31, 2017;
U.S. Prov. Ser. No. 62/449,257 filed Jan. 23, 2017;
U.S. Prov. Ser. No. 62/443,769 filed Jan. 8, 2017;
U.S. Prov. Ser. No. 62/416,403 filed Nov. 2, 2016;
U.S. Prov. Ser. No. 62/405,930 filed Oct. 9, 2016;
U.S. Prov. Ser. No. 62/375,814 filed Aug. 16, 2016;
U.S. Prov. Ser. No. 62/362,643 filed Jul. 15, 2016;
U.S. Prov. Ser. No. 62/339,810 filed May 21, 2016;
U.S. Prov. Ser. No. 62/299,453 filed Feb. 24, 2016
U.S. Prov. Ser. No. 62/287,901 filed Jan. 28, 2016;
U.S. Prov. Ser. No. 62/279,784 filed Jan. 17, 2016;
U.S. Prov. Ser. No. 62/275,241 filed Jan. 6, 2016;
U.S. Prov. Ser. No. 62/275,222 filed Jan. 5, 2016;
U.S. Prov. Ser. No. 62/259,991 filed Nov. 25, 2015;
U.S. Prov. Ser. No. 62/254,718 filed Nov. 13, 2015;
U.S. Prov. Ser. No. 62/139,754 filed Mar. 29, 2015;
U.S. Prov. Ser. No. 62/120,316 filed Feb. 24, 2015; and
U.S. Prov. Ser. No. 62/119,521 filed Feb. 23, 2015.

All of the above-referenced non-provisional, provisional and international patent applications are collectively referenced herein as "the commonly assigned incorporated applications."

FIELD

This patent specification generally relates to grasping devices for use with endoscopic surgical procedures. More particularly, some embodiments relate to surgical grasping devices and methods configured for use with portable endoscopes having a disposable cannula.

BACKGROUND

There are many medical procedures which require a tissue or other object in a human cavity to be grasped while under view of an endoscopy device. Examples of procedures include stent removal, foreign body removal, hysteroscopy endometrium biopsy, and removal of polyps.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

According to some embodiments, a disposable, single-use endoscope including a permanently mounted, integrated grasper operated under video control, comprises: a shaft having a manually operated grasper control movable relative to the shaft, a cannula extending distally from the shaft and having a working channel, and a grasper at a distal portion of the working channel; wherein: said grasper is permanently secured to said cannula and to said manually operated grasper control to move relative to the cannula with movement of the control relative to the shaft, between a retracted position at in which the grasper is within the working channel and an extended position at which the grasper protrudes distally from the channel; said grasper comprises a pair of resilient jaw portions with distal portions that are biased to move away from each other toward and to an open position as the grasper moves distally relative to the cannula toward and to its extended position; and said working channel acts on the grasper to move said distal portions of the resilient jaws toward each other and to a closed position as the grasper moves proximally relative to the cannula toward and to its retracted position.

According to some embodiments, the endoscope can further comprise one or more of the following: (a) said grasper further includes arch shaped portions from which said jaws extend distally, wherein said arch shaped portions are configured to engage an inside wall of said working channel and move the jaws toward and to said closed position as the grasper moves proximally relative to the cannula; (b) said distal portions of the jaws terminate distally in claw portions that face each other when the grasper is in its extended position and engage each other when the grasper is in its retracted position; (c). a combination with multiple-use handle, wherein the cannula includes an imaging module at a distal portion thereof and the handle includes a video screen and electronics coupled with said imaging module to control the imaging module and to cause said screen to display images taken with said imaging module; (d) in combination with said multiple-use handle of claim, wherein each of the endoscope and the handle comprises respective mechanical and electrical connectors that releasably mate mechanically with each other to form an integral unit of an endoscope and handle and to form an electronic connection between said video screen and electronics and said imaging module; (e) in combination with said multiple-use handle, wherein said mechanical and electrical connectors mate by relative motion in a direction parallel to a length of said shaft; (f) in combination with said multiple-use handle, wherein said mechanical and electrical connectors mate by relative motion in a direction transverse to length of said shaft; (g). said grasper control comprises a manually operated collar movable along a length of said shaft; (h) said grasper control comprises a manually operated tab movable along a length of said shaft; (i) said cannula is configured to rotate relative to a portion of said shaft; (j). further including a first proximal port coupled for fluid flow with a proximal portion of said working channel; (k) said cannula further includes a lumen in addition to said working channel and a second proximal port coupled for fluid flow with a proximal portion of said lumen and distal ports, for two-directional flow along a length of said cannula; (l) further including a mechanism that releasably locks the grasper in at least one of its extended and retracted position, wherein said mechanism comprises a window at a proximal portion of the cannula, a spring tab secured to said shaft and biased to engage said window when aligned therewith and thus lock said grasper against movement relative to the cannula, and a manually operated release button selectively engaging said tab to move it out of engagement with said window and thus release the grasper and cannula for relative movement therebetween; and (m). said mechanism is configured to releasably lock the grasper in its extended position.

According to some embodiments, a disposable, single-use endoscope with a cannula that includes a permanently mounted, integrated surgical tool operated under video control, comprises: a shaft having a manually operated control movable relative to the shaft, a cannula extending distally from the shaft and having a working channel and a surgical tool at a distal portion of the working channel; wherein: said surgical tool is permanently secured to said manually operated control to move relative to the cannula with movement of the control relative to the shaft, between a retracted position at which the tool is within the working channel and an extended position at which the tool protrudes distally from the channel; and said tool comprises one of: (i) a grasper comprising a pair of resilient jaw portions with distal portions biased to move away from each other and toward and to an open position as the grasper moves distally relative to the cannula toward and to its extended position wherein said working channel acts on the grasper to move said distal portions of the resilient jaws toward each other and to a closed position as the grasper moves proximally relative to the cannula toward and to its retracted position; and (ii) an injection needle for injecting medication into tissue.

According to some embodiments, the endoscope described in the immediately preceding paragraph further includes one or more of the following: (a) said tool comprises said grasper; and (b) said tool comprises said injection needle.

According to some embodiments, a method comprises: providing a disposable, single-use endoscope with a cannula that includes a permanently mounted, integrated surgical tool; inserting the endoscope in tissue or a tissue cavity or passage while the surgical tool is in a retracted position inside a working channel of the cannula, while observing the insertion path on a video screen mechanically secured releasably to the cannula, which screen receives images sent from an imaging module at a distal end of the cannula; selectively moving manually operated control relative to a shaft forming a proximal portion of the cannula to thereby move the tool toward and to an extended position at which the tool protrudes distally from the channel while observing the motion of the tool out of the working channel; wherein said tool is one of a grasper and an injection needle; and carrying out one of the steps of: (a) grasping tissue with a pair of resilient jaw portions of said grasper that are biased away from each in the extended position of the grasper by manually moving said control relative to the shaft to thereby move the grasper toward and to its retracted position into said working channel to thereby engage the jaws with an inner wall of the working channel and move them toward each into the working channel (FIG. 6D); and (b) injecting medication into tissue with said injection needle and thereafter manually moving said control relative to the shaft tot hereby move the needle toward its retracted position in the working channel.

The method can carry our step (a) or step (b).

As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning.

As used herein the terms "surgical" or "surgery" refer to any physical intervention on a patient's tissues and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments, and are therefore not to be considered limiting of the scope of this patent specification or the appended claims. The subject matter hereof will be described and explained with additional specificity and detail through the use of the accompanying drawings in which:

FIGS. 1A-1B are top and side views, respectively, of an endoscopy system having a cannula with an integrated grasper device, according to some embodiments, and FIG. 1C is a top view showing further detail of the distal tip of a grasper device integrated into an endoscopy system having a disposable cannula, according to some embodiments;

FIG. 2 is a top view of an endoscopy system having a cannula with an integrated grasper device, according to some further embodiments;

FIGS. 3A-3C are perspective views showing further details of an endoscopy system having a cannula with an integrated grasper device, according to some embodiments;

FIGS. 5A-5E are diagrams illustrating further detail of a distal tip piece and cannula for an endoscopy system having a disposable cannula with a working channel configured to accept a grasper device, according to some embodiments;

FIGS. 9B-9D are side, top and bottom views, respectively, of a single-use portion of an endoscopy system with an integrated grasper device, according to some further embodiments;

FIGS. 11A-11B are perspective diagrams of an endoscopy system having a cannula with an integrated needle, according to some embodiments.

DETAILED DESCRIPTION

Figure 4A:
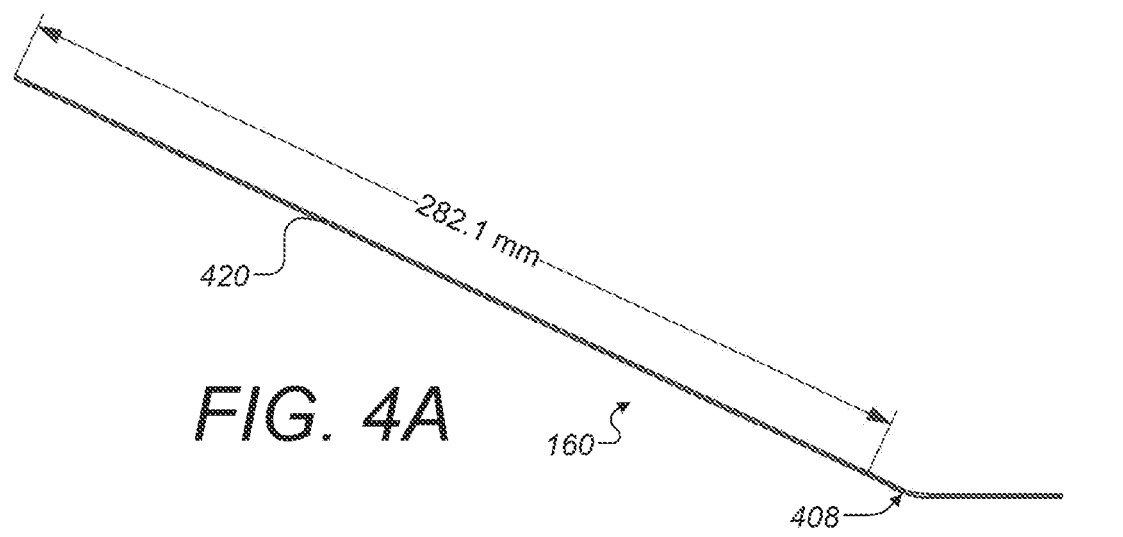
FIGS. 4A-4D are diagrams illustrating further detail of a grasper tool configured for use through the working channel of a cannula of an endoscopy system, according to some embodiments.

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

FIGS. 1A-1B are top and side views, respectively, of an endoscopy system having a cannula with an integrated grasper device, according to some embodiments. Endoscopy system 100 is configured to be handheld by hand piece 140 and includes a semi-rigid cannula 120 having an integrated grasper device 160 disposed at its distal tip 110. Imaging and illumination modules are included on distal tip 110. An electrical cable (not shown) is positioned within cannula 120 and supplies control signals and power to the camera and LED illumination modules on distal tip 110, and also transmits video image and still image data from the camera module to the hand piece 140 and display 150 for viewing by an operator. In the example shown, hand piece 140 includes control buttons 142 and 144 which can be configured for power on/off and image capture, respectively.

According to some embodiments, hand piece 140 includes a third button 148 that is configured as an exposure and/or lighting control button. Button 148 can be configured as a toggle button which circulates through a number of states, for example four states, setting the LED illumination levels and system exposure control parameters. According to some embodiments, hand piece 140 includes a rechargeable battery 146 as well as electronics for video capture, processing and display on display 150.

The cannula 120 is connected proximally to a fluid hub 130 including in this example fluid port 132. A syringe or other fluid supply device (for example as in FIG. 9A) can be used to supply (or withdraw fluid) such as saline through a fluid lumen within cannula 120 through port 132. According to some embodiments, an additional proximal port (for example as in FIG. 9A) can be connected to the device lumen and device port for infusing or withdrawing fluid from the organ or tissue into which the distal tip 110 is inserted. According to some embodiments, the outer diameter of cannula 120 is about 4.85 mm. According to some other embodiments, the outer diameter of cannula 120 can be made smaller, for example 4.65 mm. Proximal to the fluid hub 130 is a shaft 168 and a collar 170. According to some embodiments, the collar 170 is fixed to the proximal portion of grasper 160 such that it can be used to retract and extend the grasper 160 relative to the cannula 120, as will be shown and described further herein. When the operator moves collar 170 in the proximal direction the grasper 160 moves in a similar or identical proximal direction. A syringe (FIG. 9A) can be used to supply fluid, such as saline, through a fluid lumen within cannula 120 via fluid port 132. According to some embodiments, the working length L of cannula 120 including distal tip 110 is between 250 mm and 300 mm.

According to some embodiments, the system 100 is formed of a single use portion 102 and a multiple use portion 104. The portions 102 and 104 are connectable and separable via a mechanical and electrical connector (shown in FIG. 3C). According to some embodiments, the cannula 120 is semi-rigid. The cannula 120 is stiff enough so it does not collapse when actuating the grasper device 160. On the other hand, cannula 120 is flexible enough such that it can bend while it passes through curved anatomy such as male urethra or female cervix. The distal end of cannula 120 can be curved upwards at location 108 as shown in FIG. 1B. According to some embodiments, the upward bend is at least 15 degrees. According to some further embodiments, the upward bend is about 25 degrees. According to some embodiments, cannula 120 is configured to rotate about its longitudinal axis relative to handle 140, as indicated by arrow 122. A suitable rotation mechanism is described below in connection with FIG. 9E.

FIG. 1C is a top view showing further detail of the distal tip of a grasper device integrated into an endoscopy system having a disposable cannula, according to some embodiments. The distal tip of grasper 160 is shown protruding from distal end of tip 110. The distal tip of grasper 160 is formed of two opposing jaw portions 162 and 164. According to some embodiments, the jaw portions 162 and 164 are made of metal. At the distal ends of jaw portions 162 and 164 are opposing claw portions 172 and 174, respectively. Opposing claw portions 172 and 174 are configured to grasp and securely hold tissue (or other object) when the jaw portions 162 and 164 are actuated towards each other. Jaw portions 162 and 164 also include arch-shaped portions 182 and 184, respectively, that are shown just protruding distally from device channel (or working channel) opening 116. According to some embodiments, arch-shaped portions 182 and 184 are shaped such as they are pulled back into the opening 116, a force is generated to force the claw portions 172 and 714 to close towards each other, as shown by the dotted arrows. According to some embodiments, the grasper 160 is dimensioned such that the distance d from the camera module on the distal tip to the claw portions 172 and 174 allows for clear visualization of tissue or other object being grasped. According to some embodiments, the distance d is 15 mm. According to some embodiments, the grasper jaw portions 162 and 164 are made of a memory-type metal or non-metal material. According to some embodiments, jaw portions 162 and 164 are made of spring steel or nitinol alloy. According to some embodiments, the claw portions 172 and 174 when fully opened (i.e. arch portions are not engaged with opening 116) are at least 5 mm apart. According to some embodiments, claw portions 172 and 174 are shaped to "scoop" tissue when grasper 160 is configured to be used as a biopsy device.

FIG. 2 is a top view of an endoscopy system having cannula with an integrated grasper device, according to some further embodiments. The endoscopy system 200 is similar or identical to system 100 shown in FIGS. 1A-C and elsewhere herein, except that in this case cannula 120 is configured with two separate fluid lumens which are fluidly connected to two separate proximal fluid ports 232 and 234. One of the lumens is configured as a device lumen where the grasper or needle resides. According to some embodiments, one of the separate fluid lumens can be shared with the electrical cable (not shown) that supplies control signals and power, and transmits image data as described, supra. According to some other embodiments, neither of the two separate fluid lumens is used to carry the electrical cable.

FIGS. 3A-3C are perspective views showing further details of an endoscopy system having cannula with an integrated grasper device, according to some embodiments. In FIG. 3B, further detail of the distal tip 110 is shown. In particular, the view of FIG. 3B shows the camera module 330 and two LEDs 332 and 334 that are positioned below the device opening 116. According to some embodiments, tip piece 310 of distal tip 110 is arranged such that the device channel opening 116 through which the grasper device 160 (or other built-in device, such as an integrated needle) is above, or on top, of the camera module 330 rather than below the camera module. The location of the device opening 116 is slightly more distal than the surface of camera module 330, which allows for a better view by the camera module 330 of the grasper claw portions 172 and 174, or other tool tip components in cases when another type of tool device is used. The slight distal positioning of opening 116 can be achieved by a slight forward (or distal) angle of the upper portion of the front face the tip piece 310, as can also be seen in FIGS. 5A, 5B and 5D.

According to some embodiments, the grasper 160 is positioned within a lumen or "working channel" formed inside cannula 120. The device lumen or working channel can be off-center within the cross-section of the cannula 120, as is shown with working channel 516 in FIG. 5E. In cases where the cannula has a bend such as shown in FIGS. 1B and 3A at location 108, the grasper 160 (or needle) and working channel can be positioned within the cannula on the concave side of the curved cannula. Positioning an otherwise straight grasper 160 or other tool within the working channel on the concave side of the bend (above center in this case), the natural spring-like stiffness of the grasper or other tool (e.g. a needle as shown in FIGS. 11A-11B) will tend to force the grasper or tool back towards the center, or downward in this case, when exiting the device channel opening 116. The effect is that the grasper 160 or other tool will be pushed slightly toward the camera axis or toward the center of the camera field of view, making for better imaging and viewing of the tool by the operator. In cases where the shaft of the tool has a matching bend (such as shown in FIG. 4A), the bending amount can be made less than (i.e. more straight) than the bending of the cannula, which will have the same or similar effect of pushing the distal tip of the tool slightly toward the camera axis or toward the center of the camera field of view.

Also visible in FIG. 3B are two distal fluid ports 320 and 520 that are positioned on either side of device opening 116. According to some embodiments, the two distal fluid ports 320 and 520 are fluidly connected to proximal fluid port 132 in FIG. 1B, or to one of the proximal fluid ports 232 or 234 in FIG. 2.

FIG. 3C is a perspective view showing further detail with respect to connecting and separating single use portion 102 and multiple use portion 104. In particular, connector 340 on multiple use portion 104 and connector 342 on single use portion 102 are configured to make both electrical and mechanical connections between units 104 and 102.

Figure 4B:
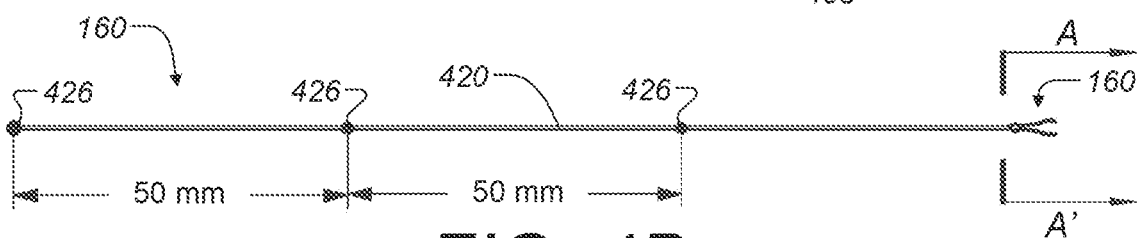
Figure 4C:
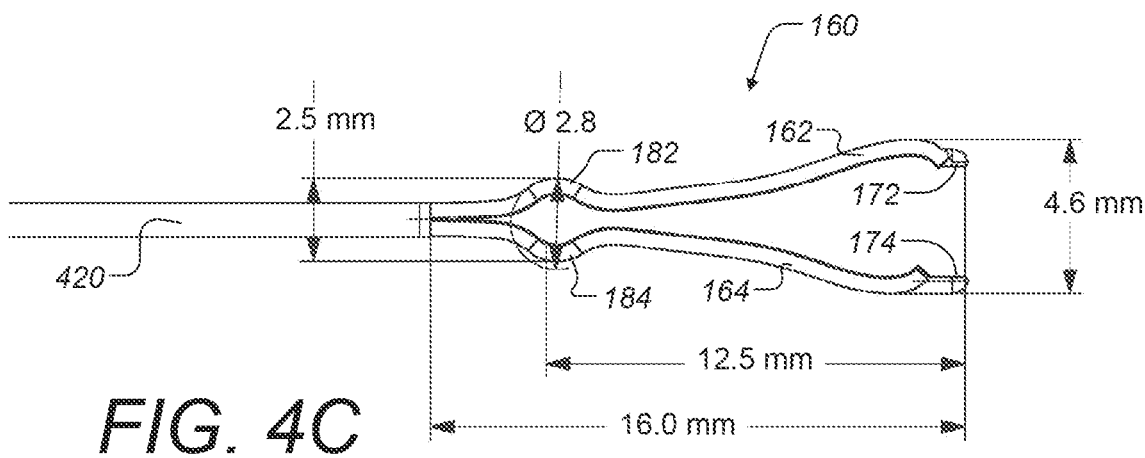
Figure 4D:
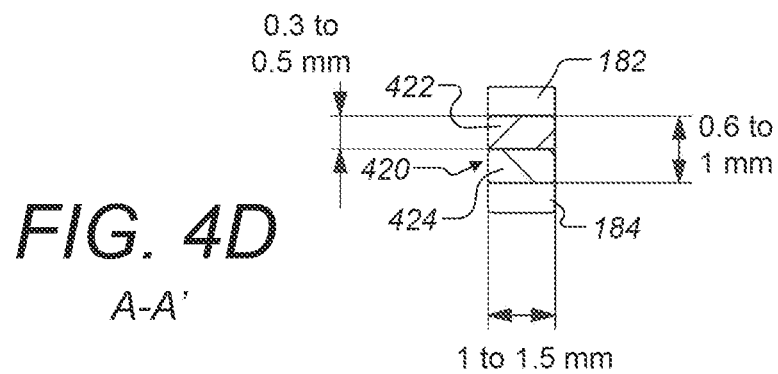

FIGS. 4A-4D are diagrams illustrating further detail of a grasper tool configured for use through the working channel of a cannula of an endoscopy system, according to some embodiments. FIG. 4A is a side view of grasper device 160 showing a main shaft 420 being bent at location 408. As described supra, the bending amount at location 408 can be made less than (i.e. straighter) than the bending of the cannula 120, such that the distal tip of the grasper 160 is pushed slightly toward the camera axis or toward the center of the camera field of view. According to some embodiments, the main shaft 20 is not pre-bent at all and is completely straight prior to insertion or after removal from cannula 120. FIG. 4B is a top view of grasper device 160, while FIG. 4C is a more detailed top view of the distal tip of grasper 160. Various dimensions are shown for this example device. FIG. 4D shows a cross section view along A-A' of FIG. 4B. The shaft 420 of grasper 160 is shown formed of two layers 422 and 424. According to some embodiments, the layers 422 and 424 of shaft 420, arch-shaped portions 182 and 184, jaw portions 162 and 164, and claw portions 172 and 174 are made of two pieces of the same material, or a single piece of material folded at the proximal end. According to some embodiments, the two pieces of material can be joined or welded at one or more locations 426 along the shaft 420 as shown in FIG. 4B. According to some embodiments, the material is a type of memory metal or memory metal alloy or a non-metal material configured to bias the jaws portions 162 and 164 to be spread apart such as shown in FIG. 4C. This allows for the claw portions 172 and 174 of grasper device 160 to be closed and opened solely by translating its position axially relative to the device channel opening 116 (shown in FIGS. 10 and 3B) as is shown in greater detail in FIGS. 6A-6D. In this way, the grasper device 160 can be relatively simple, low cost, and robust when compared to more complex arrangements such as those that include scissor-like actuation structures. According to some embodiments, each piece 422 and 424 has a cross-sectional dimension of 0.5 mm thick and 1.5 mm wide, such that the overall cross-sectional dimension of the shaft 420 is 1 mm by 1.5 mm.

FIGS. 5A-5E are diagrams illustrating further detail of a distal tip piece and cannula for an endoscopy system having a disposable cannula with a working channel configured to accept a grasper device, according to some embodiments. FIG. 5A is perspective view of distal tip piece 310. According to some embodiments, the distal tip piece 310 is formed as a separate piece and is bonded to the distal end of cannula 120 during assembly. In FIG. 5A, the camera module and LEDs are not shown for clarity. Visible are camera distal opening 530 and LED distal openings 532 and 534. Also visible in FIG. 5A are distal fluid ports 320 and 520. According to some embodiments, the device channel 516 and device channel opening 116 can also be used as a fluid channel and fluid port, respectively.

FIG. 5B is a side view of distal tip piece 310. According to some embodiments, the maximum outer diameter of tip piece 310 and cannula 120 is 6.0 mm. In the example shown, the dimensions of the outer diameter of tip piece 310 can be 5.6 mm in cases where the cannula outer diameter is about 4.85 mm. According to some embodiments, the tip piece 310 can have an outer diameter of 5.1 mm in cases where the cannula outer diameter is about 4.65 mm. Also visible in FIG. 5B is the angled upper distal face portion 510 which as described supra, provides for positioning of the device opening to be slightly more distal than the surface of camera module, which allows for a better view by the camera module of the grasper claw portions, or other tool being deployed. According to some embodiments, the face portion 510 is angled distally by about 25 degrees or 30 degrees.

FIG. 5C is a front view of distal tip piece 310. In this view the camera module 330 and LEDs 332 and 334 are shown inserted in openings 530, 532 and 534 (which are shown in FIG. 5A), respectively. The diameter of the device channel opening 116 can be 2.0 mm in cases where the outer diameter of piece 310 is 5.6 mmm, and can be 1.6 mm in cases where the outer diameter of piece 310 is 5.1 mm. FIG. 5D cross-section view along B-B' of FIG. 5C. The proximal opening 512 is dimensioned to accept and be bonded with the distal end of cannula 120. The inner diameter of opening 512 can be 4.85 mm in cases where the outer diameter of the cannula is 5.6 mm, and can be 4.65 mm in cases where the outer diameter of the cannula is 5.1 mm.

FIG. 5E is a cross section view of cannula 120. The device channel (or working channel) 516 is visible and is used to carry the grasper device 160 or another tool. Also visible are the fluid lumens 522 and 524, and cable lumen 526. According to some embodiments, fluid lumens 522 and 524 are fluidly attached to proximal fluid port 132, 232 or 234 (shown in FIGS. 1B and 2) and to distal fluid ports 320 and 520. The cable lumen 526 is used to carry the electrical cable(s) used by the camera module and LEDs. According to some embodiments, device channel 516 having an inner diameter of 2.0 mm provides adequate fluid flow capacity when the grasper shaft 420 (shown in FIG. 4D) has a dimension of 1 mm by 1.5 mm.

Figure 6A:
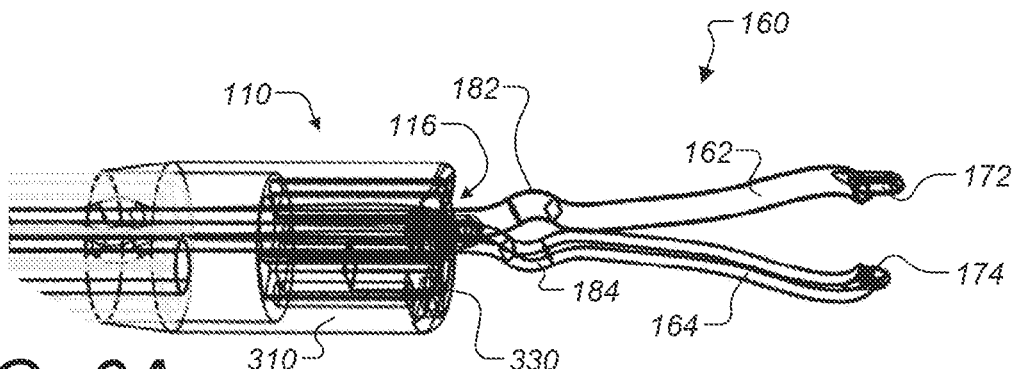
FIGS. 6A-6D and 7A-7D are two sets of diagrams illustrating a process of opening, closing, and retracting a grasper device from an endoscopy system, according to some embodiments.
Figure 6B:
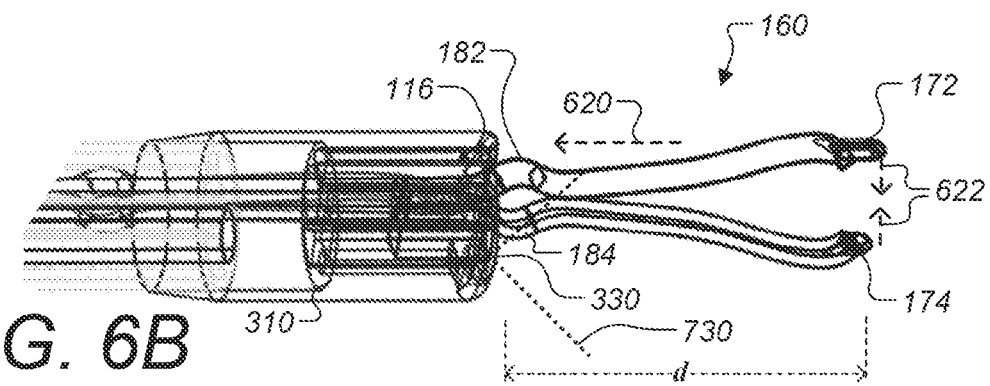
Figure 6C:
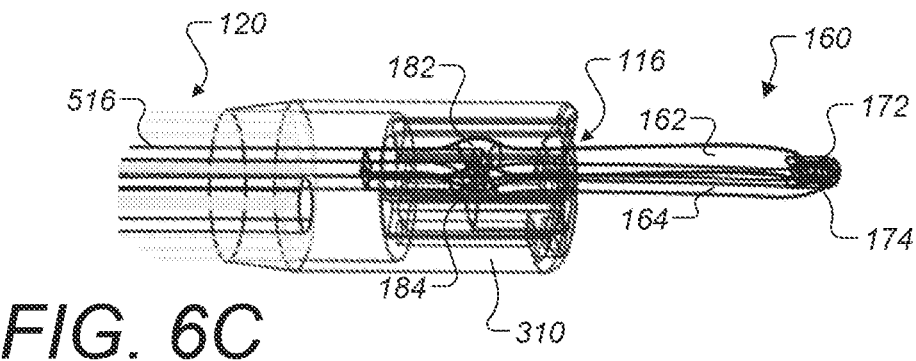
Figure 6D:
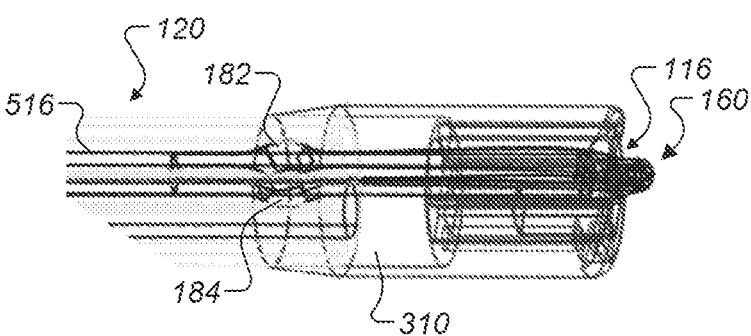
Figure 7A:
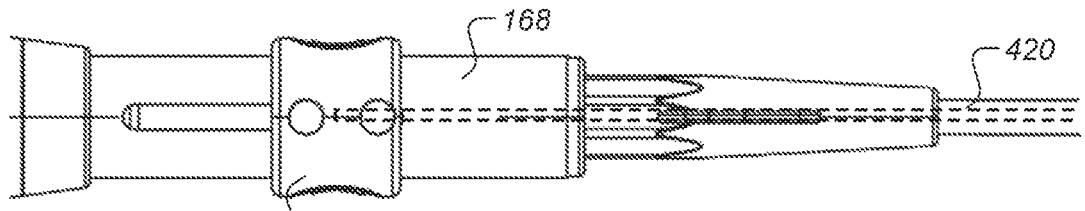

FIGS. 6A-6D and 7A-7D are two sets of diagrams illustrating a process of opening, closing, and retracting a grasper device from an endoscopy system, according to some embodiments. FIGS. 6A-6D illustrate the grasper 160 in different positions relative to the distal tip 110 while FIGS. 7A-7D show the relative positions of the collar 170 configured to control grasper 160 and shaft 168. FIGS. 6A and 7A show the grasper and collar positions, respectively, when the grasper jaw portions 162 and 164, and claw portions 172 and 174 in an "open" position. In this position, the arch shaped portions 182 and 184 protrude distally from the device opening 116 as can be seen in FIG. 6A. The collar 170 is shown in a distal position relative to shaft 168 as shown in FIG. 7A. The collar 170 is mounted or otherwise securely directly or indirectly attached to a proximal end of main shaft 420 (shown in dashed outline) of the grasper device. While the grasper 160 is in the distally protruded position from the distal opening 116 as shown in FIGS. 6A and 7A, the biased shape of the grasper device maintains the jaw portions 162 and 164 and claw portions 172 and 174 apart from each as shown.

Figure 7B:
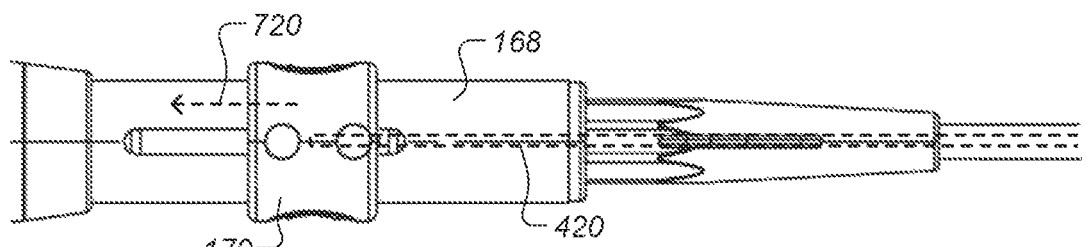

FIGS. 6B and 7B show the grasper and collar positions, respectively, when the grasper being moved proximally relative to the distal device opening 116 as indicated by dashed arrow 620 in FIG. 6B. This is accomplished by the operator manually sliding collar 170 proximally along shaft 168 as shown by dashed arrow 720 in FIG. 7B. In the position shown in FIGS. 6B and 7B, the proximal ends of arched shaped portions 182 and 184 are just beginning to engage with edge of distal opening 116. This engagement will tend for force the claw portions 172 and 174 towards each other, as shown by dashed arrows 622 in FIG. 6B. Note that due to the distanced between the device opening 116 and claw portions 172 and 174, the camera module 330 having a wide-field of view (depicted by dotted lines 730) has a good view of claw portions 172 and 174 and any tissue (or object) that might be the target of being grasped (not shown).

Figure 7C:
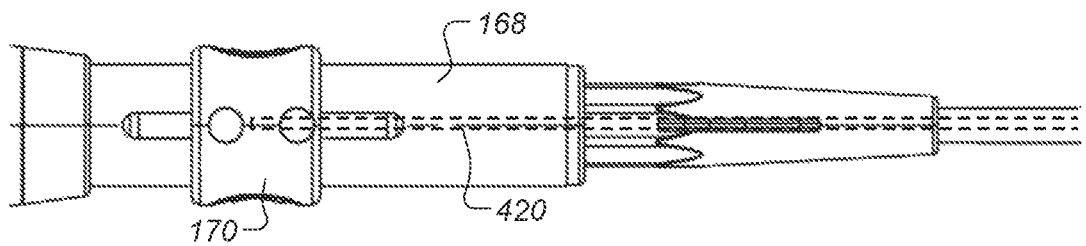

FIGS. 6C and 7C show the grasper and collar positions, respectively, when the grasper claws securely clamped towards each other. In FIG. 6C, it can be seen that the arched portions 182 and 184 are shown retracted proximally of distal device opening 116. In FIG. 7C the collar 170 is shown in a more proximal position relative to shaft 168 than in FIG. 7B. The arched portions 182 and 184 are forced together with the device channel (either within tip piece 310 or working channel 516 of cannula 120 (shown in FIG. 5E). Portions 182 and 184 being held together forces the claw portions 172 and 174 to be in a closed position and any tissue (or other object) that might be being grasped (not shown) is securely held by the claw portions.

Figure 7D:
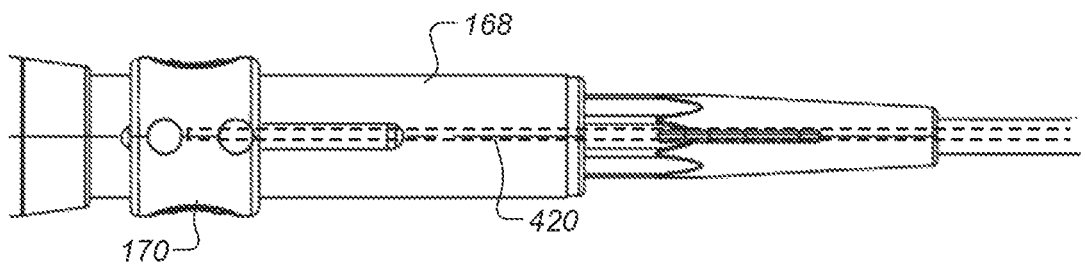

FIGS. 6D and 7D show the grasper and collar positions, respectively, when the grasper device 160 retracted even more proximally than in FIG. 6C. In FIG. 6D, the claw portions 182 and 184 are shown nearly flush with the distal face of opening 116. In FIG. 7D the collar 170 is shown retracted fully proximally along shaft 168.

Figure 8:
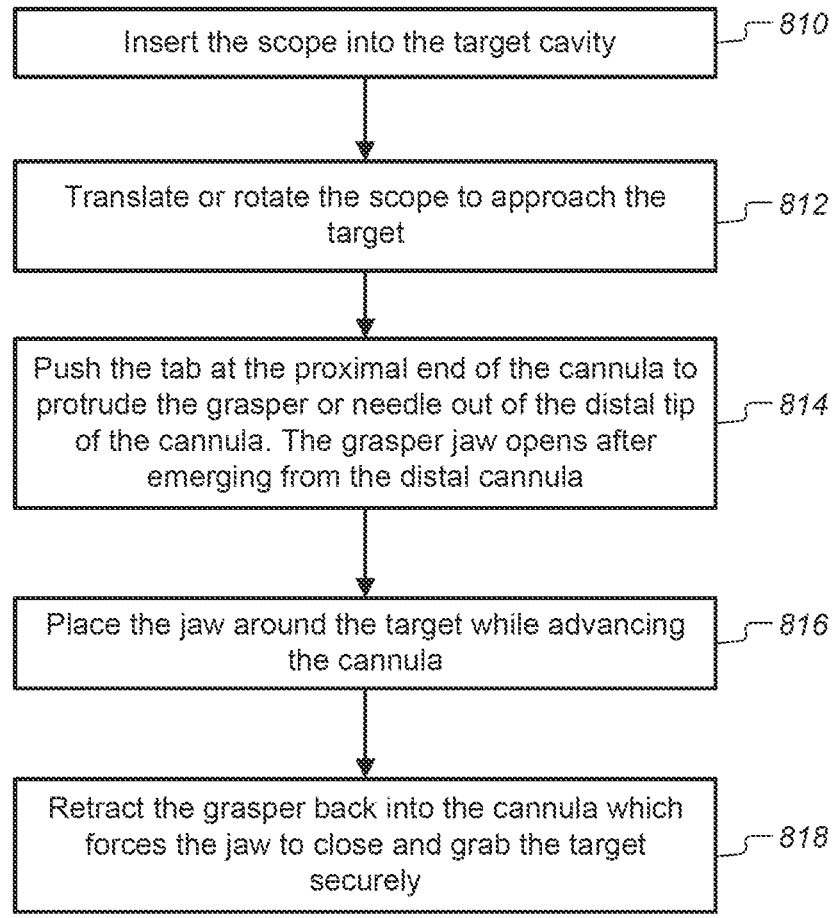
FIG. 8 is a block diagram illustrating the operation of using an endoscopy device with an integrated grasper, according to some embodiments.

FIG. 8 is a block diagram illustrating the operation of using an endoscopy device with an integrated grasper, according to some embodiments. In block 810, the endoscope (e.g. endoscopy device 100 shown in FIGS. 1A, 1B and 3A) is inserted into the target cavity while the grasper is retracted (e.g. in the position shown in FIG. 7D). Examples of target cavities include the bladder and uterus, although the endoscopy device and integrated grasper can be configured for insertion into and in operation with other cavities in the human body. In block 812 the endoscope is translated or rotated to approach the target. In block 814 the tab or collar (e.g. collar 170 shown in FIGS. 1A-B, 2, 3A, 3C and 7A-7D) at the proximal end of the cannula is pushed distally. Pushing the tab or collar distally causes the grasper or needle to protrude out of the distal tip of the cannula. The grasper jaw opens after emerging from the distal cannula (such as shown in FIG. 7A). In block 816, under direct view of camera images being shown on the integrated display (e.g. display 150 shown in FIGS. 1A-B, 2, and 3A), the claw portions of the grasper (e.g. portions 172 and 174 shown in FIGS. 10, 3B, 4C and 6A-6D) are positioned around the target while advancing the cannula. In block 818 the grasper is retracted back into the cannula which forces the jaw to close and grab the target securely, such as shown in FIGS. 6C and 6D. According to some embodiments, applications for using the endoscopy device with integrated grasper include, without limitation: stent removal, foreign body removal, hysteroscopy and endometrium biopsy. According to some embodiments, pushing the tab or collar distally can have the opposite effect and cause the grasper or needle to retract and pulling the tab or collar proximally can cause the grasper or need to extent.

Figure 9A:
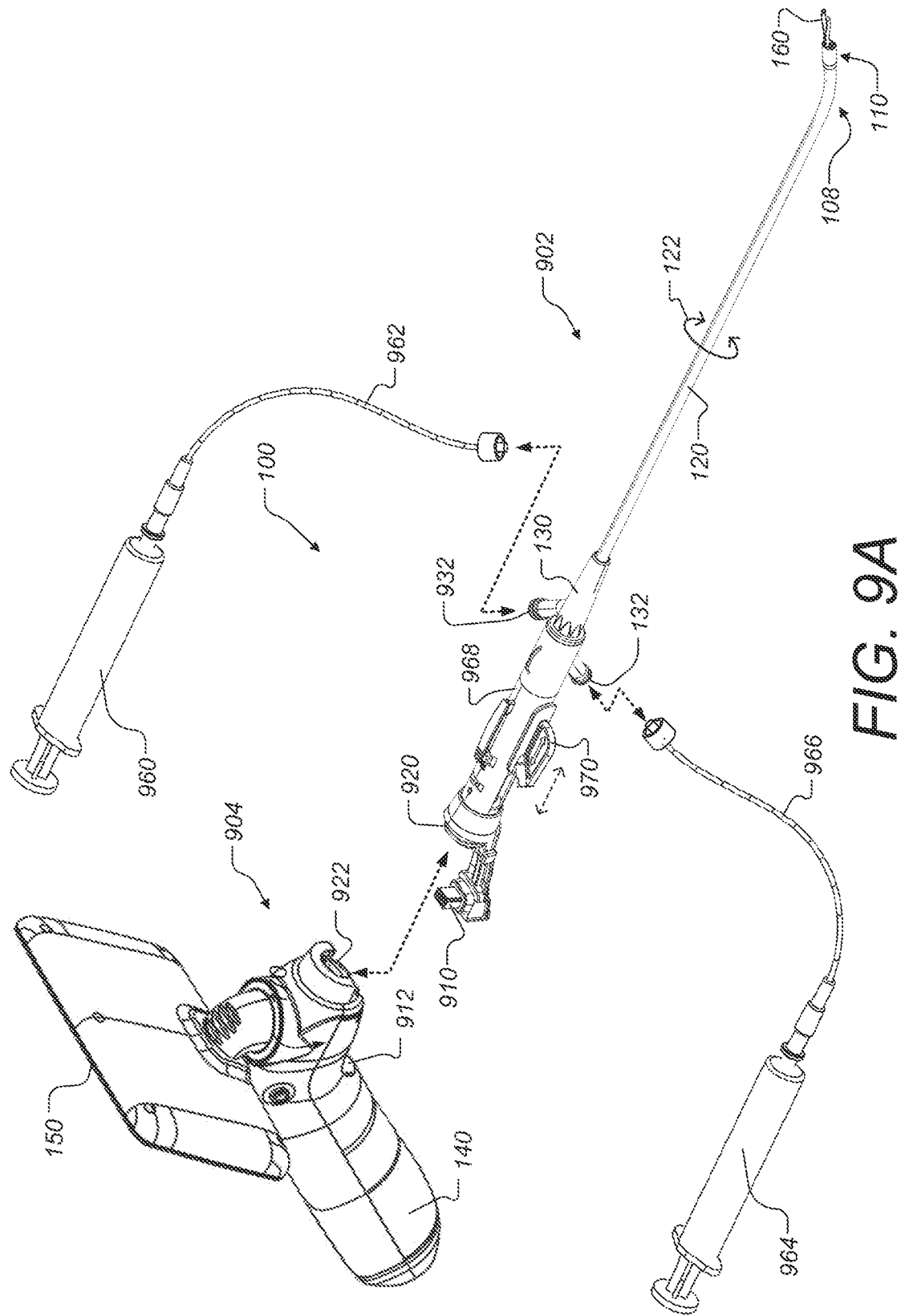
FIG. 9A is a perspective view showing an endoscopy system having cannula with an integrated grasper device, according to some further embodiments.

FIG. 9A is a perspective view showing an endoscopy system having cannula with an integrated grasper device, according to some further embodiments. In this case the single-use portion 902 is configured to be mounted and unmounted with multiple use portion 904. According to some embodiments, multiple use portion 904 is similar or identical to the multiple use portions shown and described in the commonly assigned incorporated applications. The single-use portion 902 and reusable portion 904 attach mechanically primarily via mating mechanical connectors 920 and 922, as shown by the dotted arrow. Electrical connection is made via separate mating electrical connectors 910 and 912. Instead of collar 170 sliding along shaft 168 of single use portion 102 (shown in FIGS. 1A, 1B and 3A), in FIG. 9A, tab 970 is provided that is configured to slide along shaft 968 as shown by the dashed arrow. Tab 970 is attached to the proximal end of the grasper device 160. An additional fluid port 932 is provided that is fluidly connected to the device channel (e.g. 516 in FIG. 5E) through which grasper 160 is positioned. Also shown in FIG. 9A is a fluid line 962 and syringe 960 which can be attached to fluid port 932. The syringe 960 can be used to draw fluid samples (and tissue particles suspended therein) back through the distal device opening (116), device channel (516), port 932 and into syringe 960. A second syringe 964 and fluid line 966, or other fluid delivery device, can be attached to fluid port 132 to provide in-flow fluid via ports 320 and 520 at distal tip 110 (shown in FIG. 3B). According to some embodiments, the two fluid ports 132 and 932 can provide "continuous inflow/out flow" operation. According to some embodiments, fluid or tissue debris can be withdrawn from the target cavity through port 932 while in-flow fluid (such as saline) is provide via port 132. In this way, inflow fluid distention and pressure can be controlled during the procedure. According to some embodiments, the in-flow and out-flow can be reversed between ports 132 and 932 such that port 932 is used for fluid in-flow (via device opening 116) and port 132 is used for fluid (and tissue) out-flow via distal ports 320 and 520.

The remaining components of the single use portion 902 are similar or identical to single use portion 102 and components thereof shown in FIGS. 1A, 1B, 3A, 3B, 4A-4D, 5A-5D and 6A-6D. It is understood that single use portion 902 could be substituted for single use portion 102 in any descriptions or depictions of portion 102 herein. It is also understood that multiple use portion 904 could be substituted for multiple use portion 104 in any descriptions or depictions of portion 104 herein. For example, it is understood that hand piece 140 includes two buttons configured for power on/off as well as optionally a third button configured as an exposure and/or lighting control button, as described, supra.

FIGS. 9B-9D are side, top and bottom views, respectively, of a single-use portion of an endoscopy system with an integrated grasper device, according to some further embodiments. According to some embodiments, the working length L of cannula 120 including distal tip 110 is between 250 mm and 300 mm. According to some embodiments, the working length L is 275 mm and the distance d, where the grasper 160 is fully distally protruded, is 15 mm.

Figure 9E:
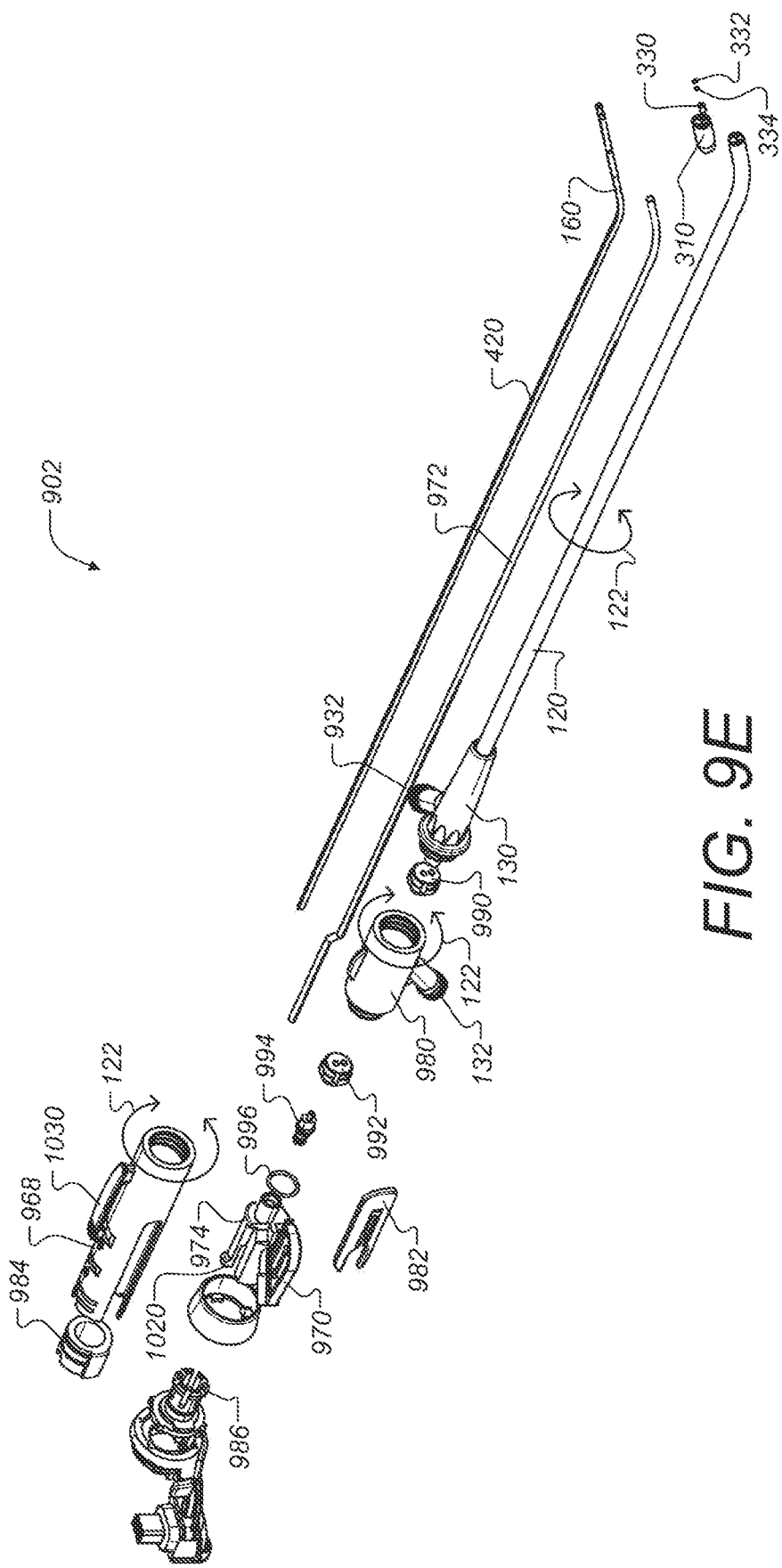
FIG. 9E is an exploded view showing further details of a single-use portion of an endoscopy system with an integrated grasper device, according to some further embodiments.
Figure 10A:
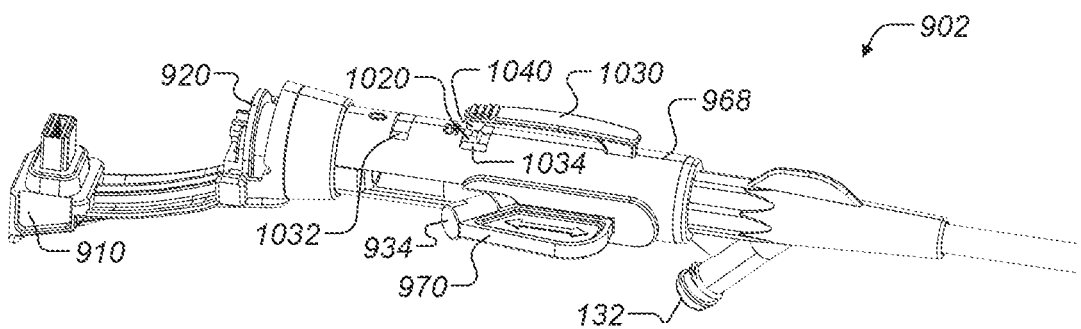
FIGS. 10A-10D are a set of diagrams illustrating a process of opening, closing, and retracting a grasper device from an endoscopy system, according to some embodiments.
Figure 10B:
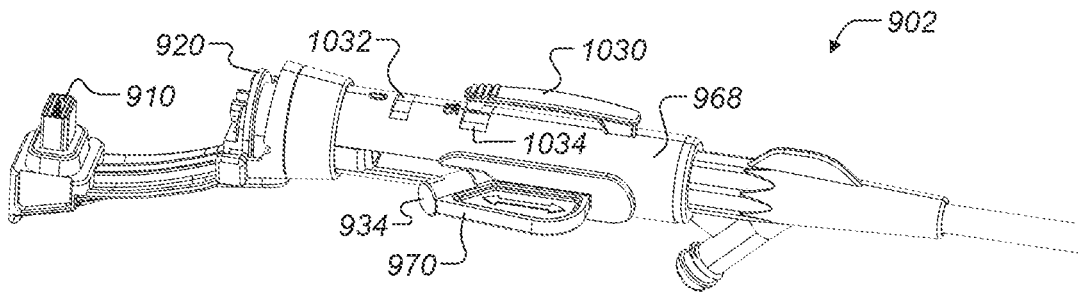
Figure 10C:
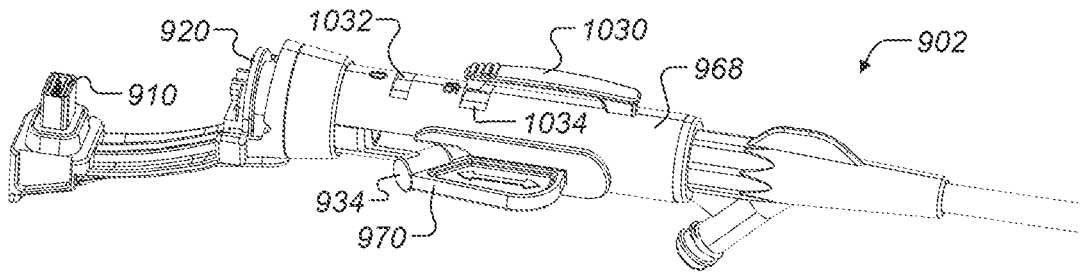
Figure 10D:
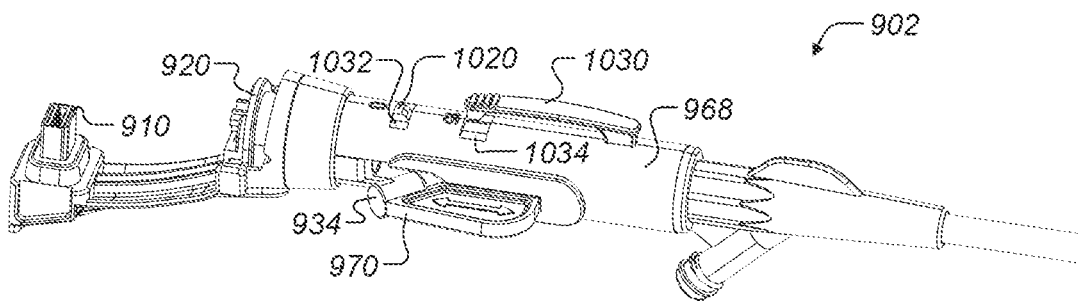

FIG. 9E is an exploded view showing further details of a single-use portion of an endoscopy system with an integrated grasper device, according to some further embodiments. At the distal end, distal tip piece 310, camera module 330 and LEDs 332 and 332 are shown. Electrical cable 972 is shown which is connected at its distal end to camera module 330 and LEDs 332 and 332. Grasper 160, including its elongated shaft 420, is also shown. Grasper 160 and cable 972 are positioned in separate lumens (516 and 526, respectively, shown in FIG. 5E) within cannula 120. At the proximal end of cannula 120, hub 130 is shown which has an inner cavity in fluid communication with fluid port 932. According to some embodiments, the device channel 516 of cannula 120 has an opening (e.g. by "skiving") within hub 130 to provide fluid communication between the device channel and fluid port 932. A silicone seal 990 is provided to prevent fluid leakage proximally of hub 130. The seal 990 has two openings through which cable 972 and shaft 420 of grasper 160 pass. The second fluid port 132 is in fluid communication with fluid hub housing 980. The cavity within housing 980 is in fluid communication with the fluid lumens of cannula 120 (lumen 522 and lumen 524 shown in FIG. 5E), for example by an opening (e.g. by "skiving"). The proximal end of hub 980 is sealed with silicone seal 992, which also has two openings through which cable 972 and shaft 420 of grasper 160 pass. Grasper end piece 994 can be a machined metallic piece that is bonded (e.g. by welding) to the proximal end of shaft 420. End piece 994, in turn, is securely mounted to slider piece 974 which includes tab 970. Slider piece 974 also includes spring tab 1020 which is shown in FIGS. 10A-10D and described in further detail, infra. Slider piece 974 is dimensioned to slide within shaft housing 968. According to some embodiments, elastomer ring 996 is provided to add additional frictional resistance to the sliding actuation of the slider piece 974 and grasper 160. A rotation socket 984 fits into shaft housing 968 proximal to the slider piece 974. The socket 984 accepts slotted axle piece 986 to allow for rotation of socket piece 984, shaft housing 968, slider piece 974, and all of the components located distally of axle piece 986 as shown by arrows 122 (and also shown in FIGS. 1A-1B, 2, 3A, 9A-9D and 11A) relative to multiple-use portion 140. According to some embodiments, rotation is confined to, slightly less than 180 degrees in either direction to avoid excessive torsional stress on cable 972.

FIGS. 10A-10D are a set of diagrams illustrating a process of opening, closing, and retracting a grasper device from an endoscopy system, according to some embodiments. FIGS. 10A-10D are similar to FIGS. 7A-7D except that tab 970 is actuated instead of collar 170. In particular, the positions of tab 970 shown in FIGS. 10A, 10B, 100 and 10D correspond to the positions of grasper 160 shown in FIGS. 6A, 6B, 6C and 6D, respectively. Note that in the example shown, single use portion 902 is configured with only one fluid port (132) instead of two fluid ports (e.g. 132 and 932 as shown in FIGS. 9A-9E). In such cases fluid port 132 can be configured as fluidly communicating with the side fluid lumens 522 and 524 and distal fluid ports 320 and 520 (shown in FIGS. 5E and 5A, respectively). According to some embodiments, device channel (516 shown in FIG. 5E) is not fluidly attached to any proximal fluid port. According to some other embodiments, an alternative proximal fluid port 934 can be configured to be fluidly attached to the device channel to provide a total of two proximal fluid ports.

According to some embodiments, the shaft 968 also includes a releasable locking mechanism as well. In the position shown in FIG. 10A, a spring tab 1020 protrudes through distal window 1034. The shape of tab 1020 has a square shaped proximal edge 1040 that engages the square shaped proximal edge of window 1034 which effectively "locks" or prevents retraction or proximal movement of grasper 160 relative to the cannula 120 (shown elsewhere). When the operator wishes to retract the grasper (or needle), the lock release button 1030 is depressed which forces the spring tab 1020 inwards though the window 1034. In the depressed state, the spring tab 1020 is no longer "locked" by the distal window 1034 and the actuation tab 970 can then be moved rearwards or proximally relative to the housing of shaft 968 which causes the grasper (or needle) to retract. According to some embodiments, the spring tab 1020 can be shaped with square edges on both proximal and distal sides which will allows for the grasper (or needle) to be releasably locked in the both the retracted position (shown in FIGS. 10D and 6D) and protruded position (shown in FIGS. 10A and 6A). In such cases, the lock release button 1030 is used to unlock the tab 1020 in either position to allow actuation of the grasper (or needle). For further details of a possible configuration of spring tab 1020 and the locking mechanism(s) see, e.g. U.S. Ser. No. 15/462,331, one of the commonly assigned incorporated applications.

FIGS. 11A-11B are perspective diagrams of an endoscopy system having cannula with an integrated needle, according to some embodiments. The needle 1160 could be used, for example, in surgical procedures to inject fluid such as a drug into the patient's tissues. Shown is single use portion 1102 configured with needle 1160 positioned in the working channel of the cannula 120 (e.g. working channel 516 in FIG. 5E). In the example shown, fluid port 132 is configured as fluidly communicating with the side fluid lumens 522 and 524 and distal fluid ports 320 and 520 (shown in FIGS. 5E and 5A, respectively). Proximal fluid port 934 next to sliding tab 970 is configured to be fluidly attached to the central channel 1162 of needle 1160.

Apart from substituting needle 1160 for grasper 160 and the configuration of fluid port 934 described supra, the rest of the single use portion 1102 is the same or similar to single use portions 902 and 102 shown and described elsewhere herein. According to some embodiments, the needle 1160 is positioned within working channel 516 (shown in FIG. 5E) which is off-center and on the concave side of the bend portion 108 of the cannula 120. Positioning an otherwise straight needle 1160 within the working channel on the concave side of the bend (above center in this case) the natural spring-like stiffness of the needle 1160 will tend to force of needle back towards the center, or downward in this case, when exiting the device channel opening 116. The effect is that the distal tip of needle 1160 will be pushed slightly toward the camera axis or toward the center of the camera field of view, making for better imaging and viewing of the tool by the operator.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What it claimed is:

1. A disposable, single-use endoscope including a permanently mounted, integrated grasper operated under video control, comprising:
    a shaft having a manually operated grasper control movable relative to the shaft, a cannula extending distally from the shaft and having a working channel, and a grasper at a distal portion of the cannula, wherein the distal portion of the cannula has a bend with a concave side;
    an imaging module that is at the distal end of the cannula and has a camera axis and a field of view;
    wherein:
    said grasper is permanently secured to said cannula and to said manually operated grasper control to move relative to the cannula with movement of the grasper control relative to the shaft, between a retracted position at in which the grasper is within the working channel and an extended position at which the grasper protrudes distally from the channel such a distal end of the grasper is distal from said imaging module;
    as said grasper moves from its retracted to its expended position, a portion of the grasper that extends distally from the cannula bends toward the imaging module and the camera axis such that the distal end of the grasper is in said field of view;
    said distal portion of the grasper comprise a pair of resilient jaw portions that are biased to move away from each other toward and to an open position as the grasper moves distally relative to the cannula toward and to its extended position;
    said working channel acts on the grasper to move the resilient jaws toward each other and to a closed position as the grasper moves proximally relative to the cannula toward and to its retracted position.

2. The disposable, single-use endoscope of claim 1 in combination with multiple-use handle, wherein the cannula includes a video screen and electronics coupled with said imaging module to control the imaging module and to cause said screen to display images taken with said imaging module.

3. The disposable, single-use endoscope in combination with said multiple-use handle of claim 2, wherein each of the endoscope and the handle comprises respective mechanical and electrical connectors that releasably mate mechanically with each other to form an integral unit of an endoscope and handle and to form an electronic connection between said video screen and electronics and said imaging module.

4. The disposable, single-use endoscope of claim 1, in which said grasper control comprises a manually operated tab.

5. The disposable, single-use endoscope of claim 2, in which said cannula is configured to rotate relative to said handle.

6. The disposable, single-use endoscope of claim 1, further including a first fluid channel in said cannula and a first proximal port coupled for fluid flow with said first fluid channel.

7. The disposable, single-use endoscope of claim 6, in which said cannula further includes a second fluid channel and a second fluid port coupled for fluid flow with said second fluid channel.

8. The disposable, single-use endoscope of claim 1, further including a mechanism that releasably locks the grasper in at least one of its extended and retracted position, wherein said mechanism comprises a window at a proximal portion of the shaft, a spring tab secured to said shaft and biased to engage said window when aligned therewith and thus lock said grasper against movement relative to the cannula, and a manually operated release button selectively engaging said tab to move it out of engagement with said window and thus release the grasper and cannula for relative movement therebetween.

9. The disposable, single-use endoscope of claim 8, in which said mechanism is configured to releasably lock the grasper in its extended position.

10. A disposable, single-use endoscope with a cannula that includes a permanently mounted, integrated surgical tool operated under video control, comprising:
an elongated cannula and a manually operated control movable relative to the cannula, a working channel in the cannula, a surgical tool at a distal portion of the cannula, and an imaging module at the distal end of the cannula, said imaging module having a field of view and a camera axis;
wherein:
said surgical tool is permanently secured to said manually operated control to move distally and proximally relative to the cannula with movement of the control relative to the cannula, between a retracted position at which the tool is within the working channel and an extended position at which the tool protrudes distally from the channel; and
said surgical tool comprises a grasper comprising a pair of resilient jaw portions that include: (i) distal portions biased to move away from each other and toward and into an open position as the grasper moves distally relative to the cannula toward and into its extended position and terminate in claws that are spaced from each other when the grasper is in its extended position and engage each other when the grasper is in its retracted position; and (ii) proximal portions that are at a proximal end of the grasper and are arch-shaped and configured to engage an inside wall of said working channel and move the distal portions toward and into engagement with each other as the grasper moves proximally relative to the cannula;
wherein as the grasper moves distally relative to the cannula toward and to its extended position said grasper bends to move the distal portions of the resilient jaws toward the imaging module and the camera axis such that said claws are in said field of view.

* * * * *